US012697030B2

(12) United States Patent
Lee et al.

(10) Patent No.: US 12,697,030 B2
(45) Date of Patent: Aug. 4, 2026

(54) BIO IMAGING SYSTEMS AND BIO IMAGING METHODS

(71) Applicant: Samsung Electronics Co., Ltd., Suwon-si (KR)

(72) Inventors: Gae Hwang Lee, Seongnam-si (KR); Youngjun Yun, Seongnam-si (KR); Jong Won Chung, Hwaseong-si (KR); Hyun Bum Kang, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 163 days.

(21) Appl. No.: 18/342,796

(22) Filed: Jun. 28, 2023

(65) Prior Publication Data

US 2023/0329560 A1 Oct. 19, 2023

Related U.S. Application Data

(63) Continuation of application No. 17/104,599, filed on Nov. 25, 2020, now Pat. No. 11,717,168.

(30) Foreign Application Priority Data

Jul. 20, 2020 (KR) ........................ 10-2020-0089587

(51) Int. Cl.
*A61B 5/00* (2006.01)

(52) U.S. Cl.
CPC ............ *A61B 5/0086* (2013.01); *A61B 5/004* (2013.01); *A61B 5/0059* (2013.01); *A61B 5/0075* (2013.01); *A61B 5/489* (2013.01); *A61B 5/6876* (2013.01); *A61B 5/0033* (2013.01); *A61B 2562/0233* (2013.01); *A61B*

*2562/046* (2013.01); *A61B 2562/164* (2013.01); *A61B 2562/166* (2013.01)

(58) Field of Classification Search
None
See application file for complete search history.

(56) References Cited

U.S. PATENT DOCUMENTS 8,405,832 B2 3/2013 Schmaelzle et al.
9,936,574 B2 4/2018 Rogers et al.
(Continued)

FOREIGN PATENT DOCUMENTS

CN 109698211 A 4/2019
CN 110120400 A 8/2019
(Continued)

OTHER PUBLICATIONS

K. Cnops et al., '8.4% efficient fullerene-free organic solar cells exploiting long-range exciton energy transfer' *Nature Communications*, 5:3406, 2014.
(Continued)

*Primary Examiner* — Keith M Raymond
*Assistant Examiner* — Michael S Kellogg
(74) *Attorney, Agent, or Firm* — Harness, Dickey & Pierce, P.L.C.

(57) ABSTRACT

A bio imaging system includes a plurality of light emitters configured to irradiate light, and a plurality of sensors configured to detect light reflected by an internal tissue of a living body. Each sensor includes a plurality of photo-detecting elements having different absorption peak wavelengths in relation to each other.

20 Claims, 20 Drawing Sheets

220

(56) References Cited

U.S. PATENT DOCUMENTS

| | | | |
|---|---|---|---|
| 10,644,186 B2 | 5/2020 | Yoo et al. | |
| 10,786,186 B2 | 9/2020 | Heo et al. | |
| 10,976,195 B2 | 4/2021 | Leem et al. | |
| 11,107,860 B2 | 8/2021 | Lee et al. | |
| 11,435,227 B2 | 9/2022 | Leem et al. | |
| 11,690,542 B2 | 7/2023 | Heo et al. | |
| 11,785,789 B2 | 10/2023 | Lee et al. | |
| 2012/0165759 A1 | 6/2012 | Rogers et al. | |
| 2016/0049448 A1 | 2/2016 | Lee et al. | |
| 2016/0380032 A1 | 12/2016 | Park et al. | |
| 2017/0337412 A1 | 11/2017 | Bhat et al. | |
| 2017/0337413 A1 | 11/2017 | Bhat et al. | |
| 2018/0000387 A1* | 1/2018 | Heo | A61B 5/14532 |
| 2019/0120689 A1* | 4/2019 | Leem | G06V 10/143 |
| 2019/0343395 A1* | 11/2019 | Cussac | A61B 5/0261 |

FOREIGN PATENT DOCUMENTS

| | | | |
|---|---|---|---|
| EP | 2413263 A1 | 2/2012 | |
| KR | 10-1667917 B1 | 10/2016 | |
| KR | 10-2018-0003227 A | 1/2018 | |
| KR | 10-2019-0114386 A | 10/2019 | |
| KR | 10-2019-0119382 A | 10/2019 | |

OTHER PUBLICATIONS

Ying Zheng and Jiangeng Xue, 'Organic Photovoltaic Cells Based on Molecular Donor-Acceptor Heterojunctions' *Polymer Reviews,* 50:420-453, 2010.

Extended European Search Report dated May 10, 2021 for corresponding European Application No. 20209793.7.

Chinese Office Action dated Mar. 5, 2025 for corresponding Chinese Application No. 202110676447.0, and English-language translation thereof.

Korean Office Action dated May 4, 2025 for corresponding Korean Patent Application No. 10-2020-0089587, and English-language translation thereof.

* cited by examiner

<u>220</u>

<u>220</u>

BIO IMAGING SYSTEMS AND BIO IMAGING METHODS

CROSS-REFERENCE TO RELATED APPLICATIONS

This application is a continuation of U.S. application Ser. No. 17/104,599, filed Nov. 25, 2020, which claims priority to and the benefit, under 35 U.S.C. § 119, of Korean Patent Application No. 10-2020-0089587 filed in the Korean Intellectual Property Office on Jul. 20, 2020, the entire contents of each of which are incorporated herein by reference.

BACKGROUND

1. Field

Bio imaging systems and bio imaging methods are disclosed.

2. Description of the Related Art

Various equipment for obtaining images of internal tissue of the living body such as a blood vessel has been used for various purposes such as medical care or security. For example, an image of the internal tissues of a living body may be effectively obtained by irradiating the skin with a light source and using a camera.

However, since the image obtained by this method may include all images of skin and blood vessels positioned at the point where light passes, there is a limitation in selectively obtaining an image of a target internal body tissue.

SUMMARY

Some example embodiments provide a bio imaging system capable of obtaining an image of an internal body tissue positioned at a specific depth.

Some example embodiments provide a bio imaging method using the bio imaging system.

According to some example embodiments, a bio imaging system includes a plurality of light emitters configured to irradiate light, and a plurality of sensors configured to detect light scattered or reflected by an internal tissue of a living body, wherein each sensor of the plurality of sensors includes a plurality of photo-detecting elements, the plurality of photo-detecting elements having different absorption peak wavelengths in relation to each other.

The plurality of photo-detecting elements may be stacked on each other.

Each absorption peak wavelength of the plurality of photo-detecting elements may be within a visible wavelength spectrum or an infrared wavelength spectrum.

Each absorption peak wavelength of the plurality of photo-detecting elements may be within about 450 nm to about 1200 nm.

A difference between absorption peak wavelengths of the plurality of photo-detecting elements may be greater than or equal to about 10 nm.

Each emission spectrum of each light emitter of the plurality of light emitters may include respective absorption peak wavelengths of the plurality of photo-detecting elements.

The plurality of photo-detecting elements of each sensor of the plurality of sensors may include a first photo-detecting element and a second photo-detecting element stacked on each other, the first photo-detecting element may include a first absorption layer configured to selectively detect light in a first wavelength spectrum (e.g., first absorption spectrum) having a first absorption peak wavelength, and the second photo-detecting element may include a second absorption layer configured to selectively detect light in a second wavelength spectrum (e.g., second absorption spectrum) having a second absorption peak wavelength that is longer than the first absorption peak wavelength.

Each sensor of the plurality of sensors may include a first electrode on one surface of the first absorption layer of the plurality of photo-detecting elements of the sensor, a second electrode on one surface of the second absorption layer of the plurality of photo-detecting elements of the sensor, and a third electrode facing the first electrode and the second electrode, respectively, and between the first absorption layer and the second absorption layer, wherein the third electrode may be a common electrode of the first photo-detecting element and the second photo-detecting element.

Each sensor of the plurality of sensors may further include a third photo-detecting element stacked on the second photo-detecting element, and insulating layers between the first photo-detecting element and the second photo-detecting element, and between the second photo-detecting element and the third photo-detecting element, and the third photo-detecting element may include a third absorption layer configured to detect light in a third wavelength spectrum (e.g., a third absorption spectrum) having a third absorption peak wavelength that is longer than the second absorption peak wavelength.

The bio imaging system may further include a stretchable substrate configured to support the plurality of light emitters and the plurality of sensors.

The stretchable substrate may include a plurality of first regions having a first elastic modulus and a second region between adjacent first regions of the plurality of first regions and having a second elastic modulus, the first elastic modulus being higher than the second region, and the plurality of light emitters and the plurality of sensors may be in separate, respective first regions of the plurality of first regions of the stretchable substrate.

The bio imaging system may include a light emitter-sensor array in which the plurality of light emitters and the plurality of sensors are alternately arranged.

The bio imaging system may include a light emitter array in which the plurality of light emitters are arranged, and a sensor array in which the plurality of sensors are arranged, and the light emitter array and the sensor array may be disposed at different heights from the stretchable substrate.

The bio imaging system may further include a light diffusion layer between the light emitter array and the sensor array.

The bio imaging system may further include at least one of a driving unit (e.g., processing circuitry) or a display unit (e.g., display panel).

According to some example embodiments, a bio imaging method includes fixing the bio imaging system on a skin of a living body, activating the plurality of light emitters to irradiate light to the skin, and selectively sensing light scattered or reflected by the internal tissue of the living body through the skin in each photo-detecting element of a plurality of photo-detecting elements of at least one sensor of the plurality of sensors according to the wavelength spectrum of the light scattered and reflected to obtain a plurality of images.

The bio imaging method may further include extracting differences between the plurality of images to obtain a plurality of "depth" images of the internal tissue of the living body according to depth from the surface of the skin.

The plurality of photo-detecting elements of each sensor of the plurality of sensors may include a first photo-detecting element configured to detect light in a first absorption spectrum having a first absorption peak wavelength, a second photo-detecting element configured to detect light in a second absorption spectrum having a second absorption peak wavelength that is longer than the first absorption peak wavelength, and a third photo-detecting element configured to detect light in a third absorption spectrum having a third absorption peak wavelength that is longer than the second absorption peak wavelength, wherein the obtaining of the plurality of depth images of the internal tissue of the living body according to depth from the surface of the skin may include extracting a first depth image of the internal tissue of the living body at a first depth from the surface of the skin, from a first difference between a first image obtained by the first photo-detecting element and a second image obtained by the second photo-detecting element, and extracting a second depth image of the internal tissue of the living body at a second depth that is deeper than the first depth, from a second difference between a third image obtained by the third photo-detecting element and the second image obtained by the second photo-detecting element.

The bio imaging method may further include combining the plurality of depth images of the internal tissue of the living body to obtain a three-dimensional image of the internal tissue of the living body.

The internal tissue of the living body may include blood vessels.

High-resolution images of internal tissues located at a specific depth may be obtained.

DETAILED DESCRIPTION

Figure 1:
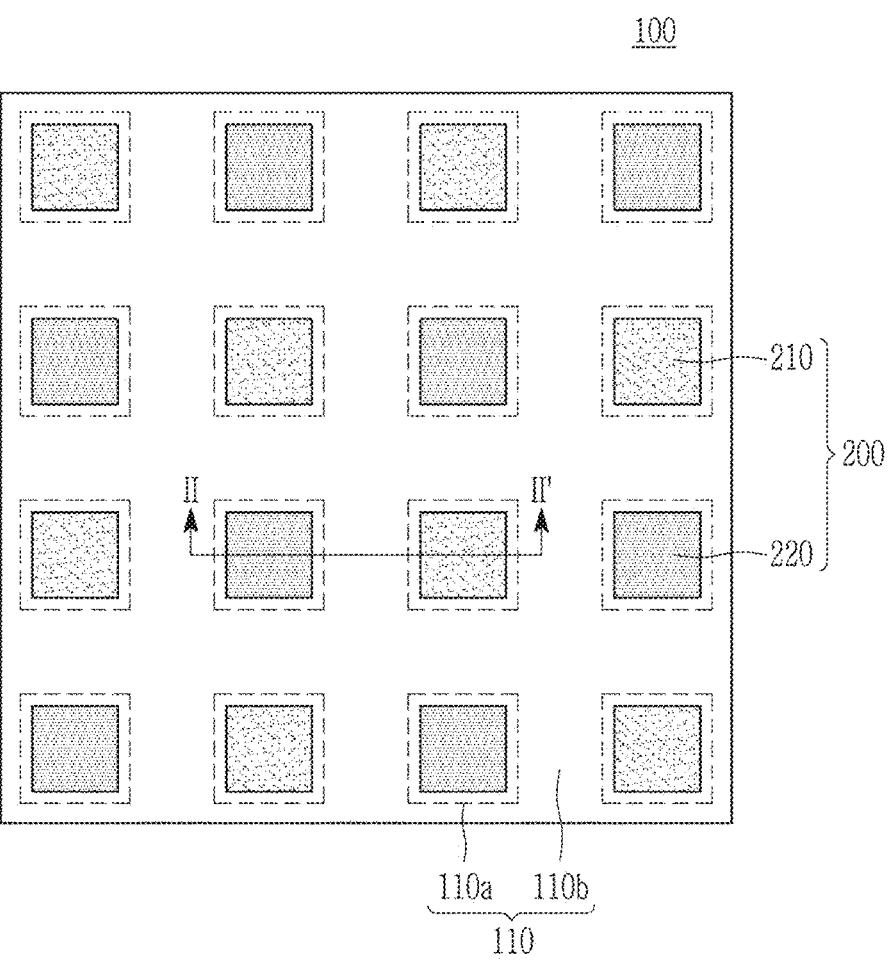
FIG. 1 is a plan view showing an example of a bio imaging system according to some example embodiments.

Hereinafter, implementation examples will be described in detail so that those of ordinary skill in the art can easily implement them. However, the structure that is actually applied may be implemented in various different forms and is not limited to example embodiments described herein.

In the drawings, the thickness of layers, films, panels, regions, etc., are exaggerated for clarity. It will be understood that when an element such as a layer, film, region, or substrate is referred to as being "on" another element, it may be directly on the other element or intervening elements may also be present. In contrast, when an element is referred to as being "directly on" another element, there are no intervening elements and/or spaces present (e.g., the elements are in direct contact with each other).

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

Hereinafter, a bio imaging system according to some example embodiments will be described.

A bio imaging system is an imaging device capable of providing spatial distribution information such as a location, shape, size, and/or thickness of an internal tissue of the living body such as a blood vessel.

Figure 2:
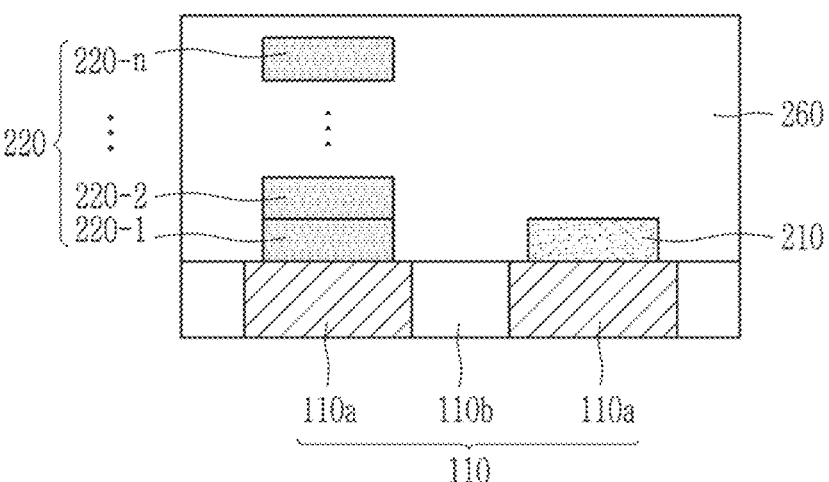
FIG. 2 is a cross-sectional view of an example of the bio imaging system of FIG. 1 taken along line II-II'.
Figure 3A:
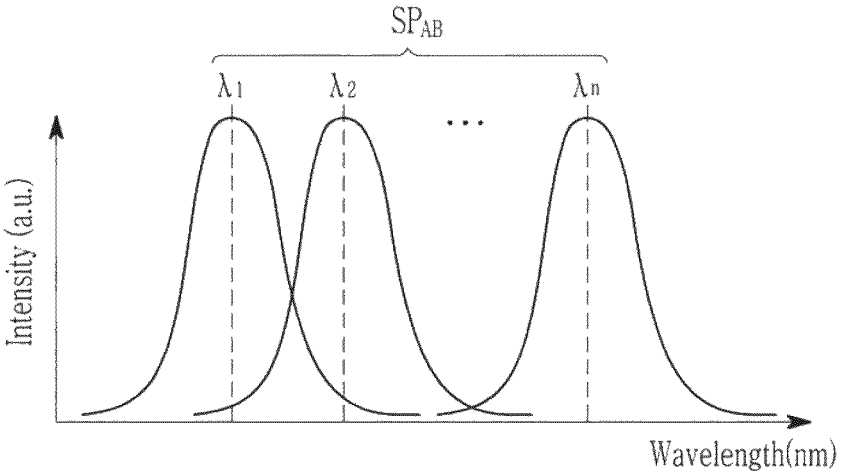
FIGS. 3A and 3B are graphs showing an example of an emission spectrum of a light emitter and a sensor of the bio imaging system of FIGS. 1 and 2.
Figure 3B:
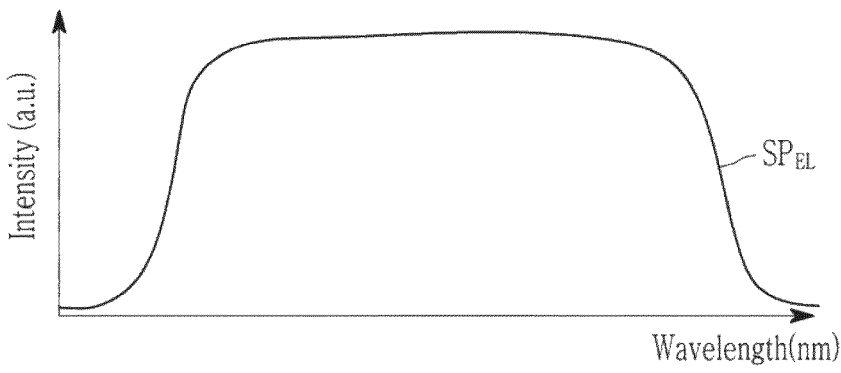

FIG. 1 is a plan view showing an example of a bio imaging system according to some example embodiments, FIG. 2 is a cross-sectional view of an example of the bio imaging system of FIG. 1 taken along line II-II', and FIGS. 3A and 3B are graphs showing an example of an emission spectrum of a light emitter and a sensor of the bio imaging system of FIGS. 1 and 2.

Referring to FIGS. 1 and 2, a bio imaging system 100 according to some example embodiments includes a substrate 110; a light emitter-sensor array 200 including a plurality of light emitters 210 and a plurality of sensors 220 arranged on the substrate 110; and optionally an encapsulation film 260 covering the light emitter-sensor array 200.

The substrate 110 may be disposed under the light emitter-sensor array 200 to support (e.g., structurally support) the plurality of light emitters 210 and the plurality of sensors 220. Structurally supporting the light emitters 210 and sensors 220 may include holding the light emitters 210 and sensors 220 in a particular structural and/or spatial arrangement in the bio imaging system 100. The substrate 110 may be a portion that is in contact with a living body or disposed close to a living body, and may have high light transmittance so that light irradiated from the light emitter 210 and light reflected by an internal tissue of the living body may pass. The substrate 110 may have for example, light transmittance of greater than or equal to about 70%, greater than or equal to about 75%, greater than or equal to about 80%, greater than or equal to about 85%, greater than or equal to about 90%, greater than or equal to about 95%, greater than or equal to about 97%, greater than or equal to about 98%, or greater than or equal to about 99%.

For example, the substrate 110 may be a stretchable substrate. The stretchable substrate may respond flexibly to external forces or external movements such as twisting, pressing, and pulling, and may be easily restored to its original state.

The stretchable substrate may include or made of a stretchable material such as an elastomer, and the stretchable material may include an organic elastomer, an organic/inorganic elastomer, an inorganic elastomer-like material, or a combination thereof. The organic elastomer or the organic/inorganic elastomer may be, for example, a substituted or unsubstituted polyorganosiloxane such as polydimethylsiloxane, an elastomer including substituted or unsubstituted butadiene moiety such as styrene-ethylene-butylene-styrene, an elastomer including a urethane moiety, an elastomer including an acrylic moiety, an elastomer including an olefin moiety, or a combination thereof, but is not limited thereto. The inorganic elastomer-like material may include an elastic ceramic, solid metal, liquid metal, or a combination thereof, but is not limited thereto.

The substrate 110 may include regions having different stiffness, for example, a first region 110a having relatively high stiffness and a second region 110b having a relatively low stiffness than the first region 110a. Herein, the stiffness may indicate a degree of resistance to deformation when a force is applied from the outside. Relatively high stiffness may mean that the resistance to deformation is relatively large, so that deformation is small, while relatively low stiffness may mean that the resistance to deformation is relatively small, so that the deformation is large.

The stiffness may be evaluated from an elastic modulus, and a high elastic modulus may mean high stiffness and a low elastic modulus may mean low stiffness. The elastic modulus may be, for example, a Young's modulus. The elastic modulus of the first regions 110a may be higher than the elastic modulus of the second region 110b. A difference between elastic moduli of the first regions 110a and the second region 110b of the substrate 110 may be about 100 times or more, and the elastic modulus of the first regions 110a may be about 100 times higher than the elastic modulus of the second region 110b. The difference between the elastic modulus of the first regions 110a and the second region 110b may be about 100 to 100,000 times within the above range, and the elastic modulus of the first regions 110a may be about 100 times to about 100,000 times higher than the elastic modulus of the second region 110b, but is not limited thereto. For example, the elastic modulus of the first regions 110a may be about $10^7$ Pa to about $10^{12}$ Pa, and the elastic modulus of the second region 110b may be greater than or equal to about $10^2$ Pa and less than about $10^7$ Pa, but is not limited thereto.

Elongation rates of the first regions 110a and the second region 110b of the substrate 110 may be different due to the aforementioned difference in stiffness, and the elongation rate of the second region 110b may be higher than the elongation rate of the first regions 110a. Herein, the elongation rate may be a percentage of the length change that is increased to a breaking point with respect to the initial length. For example, the elongation rate of the first regions 110a of the substrate 110 may be less than or equal to about 5%, within the range, about 0% to about 5%, about 0% to about 4%, about 0% to about 3%, about 0% to about 2%, about 0% to about 1%, about 0.5% to about 5%, about 0.5% to about 4%, about 0.5% to about 3%, about 0.5% to about 2%, or about 1% to about 2%. For example, the elongation rate of the second region 110b of the substrate 110 may be greater than or equal to about 10%, within the range, about 10% to about 300%, about 10% to about 200%, about 10% to about 100%, about 10% to about 90%, about 10% to about 80%, about 10% to about 70%, about 10% to about 60%, about 10% to about 50%, about 10% to about 40%, about 20% to about 70%, about 20% to about 60%, about 20% to about 50%, or about 20% to about 40%.

A plurality of first regions 110a of the substrate 110 may have an island-shape separated from each other, and the light emitter 210 and the sensor 220 which are described later are disposed on each first region 110a of the substrate 110.

The second region 110b of the substrate 110 may be a region other than the plurality of first regions 110a and may be continuously connected thereto and thus may be between adjacent first regions 110a. The second region 110b of the substrate 110 may be a region providing stretchability and due to its relatively low stiffness and high elongation rate, the second region 110b of the substrate 110 may flexibly respond to external forces or external movements such as twisting and pulling, and may be easily restored to its original state.

For example, the first regions 110a and the second region 110b of the substrate 110 may have different shapes. For example, the first regions 110a of the substrate 110 may be flat and the second region 110b may include a two-dimensional or three-dimensional stretchable structure. The two-dimensional or three-dimensional stretchable structure may have, for example, a wavy shape, a wrinkle shape, a pop-up shape, or a non-coplanar mesh shape, but is not limited thereto.

For example, the first regions 110a and the second region 110b of the substrate 110 may include different materials. For example, the first regions 110a of the substrate 110 may include an inorganic material, an organic material, and/or an organic/inorganic material having relatively high stiffness and a low elongation rate, and the second region 110b of the substrate 110 may include an inorganic material, an organic material, and/or an organic/inorganic material having a relatively low stiffness and high elongation rate. For example, the first regions 110a of the substrate 110 may include or made of an organic material such as polycarbonate, polymethylmethacrylate, polyethyleneterephthalate, polyethylenenaphthalate, polyimide, polyamide, polyamide-imide, polyethersulfone, or a combination thereof, a carbon structure such as diamond carbon, and the second region 110b of the substrate 110 may include or made of an organic or organic/inorganic elastomer such as a substituted or unsubstituted polyorganosiloxane such as polydimethylsiloxane, an elastomer including a substituted or unsubstituted butadiene moiety such as styrene-ethylene-butylene-styrene, an elastomer including a urethane moiety, an elastomer including an acrylic moiety, an elastomer including an olefin moiety, or a combination thereof; an inorganic elastomer-like material such as ceramic, a solid metal, a liquid metal, or a combination thereof, but they are not limited thereto.

For example, the first regions 110a and the second region 110b of the substrate 110 may be formed with the same material, and may have different stiffness by different conditions such as polymerization degrees and/or curing degrees. For example, the substrate 110 may have the first regions 110a having a relatively high stiffness and the second region 110b having a relatively low stiffness which are formed by varying the polymerization degrees, types and contents of curing agents, and/or curing temperatures, based on polydimethylsiloxane.

In this way, the substrate 110 includes first regions 110a having a relatively high stiffness and a low elongation rate, and a second region 110b having a relatively low stiffness and a high elongation rate, and includes a light emitter 210 and a sensor 220 which are disposed in the first regions 110a, and thereby even when a large external force or movement is applied to the substrate 110, the light emitter 210 and sensor 220 in the first regions 110a may receive relatively less strain and thus, the light emitter 210 and sensor 220 may be prevented from being damaged or destroyed by excessive strain.

A light emitter-sensor array 200 is disposed on the substrate 110. The light emitter-sensor array 200 includes a plurality of light emitters 210 and a plurality of sensors 220. The light emitter-sensor array 200 (e.g., the plurality of light emitters 210 and the plurality of sensors 220) may be on separate, respective first regions 110a, for example as shown in FIG. 1. As shown in FIG. 1, the plurality of light emitters 210 and the plurality of sensors 220 may be, for example, alternately arranged along rows and/or columns. In the drawings, the shape, size, and number of the light emitter 210 and the sensor 220 are illustrated as an example, but the shape, size, and number of the light emitter 210 and the sensor 220 may be variously changed. For example, the light emitter 210 and the sensor 220 may have a dimension of several to hundreds of micrometers. For example, the light emitter 210 and the sensor 220 may each independently have a width, length, and thickness of greater than or equal to about 1 μm and less than 1000 μm, and within the range, may have a width, length, and thickness of about 10 μm to about 800 μm, about 10 μm to about 700 μm, about 10 μm to about 600 μm, or about 10 μm to about 500 μm, but is not limited thereto. For example, one to three hundreds of light emitters 210 and sensors 220 may be included, respectively.

The light emitter 210 may be configured to irradiate (e.g., emit) light supplied to (e.g., to irradiate) internal tissue of the living body through a skin, and may include, for example, a light-emitting element such as an inorganic light emitting diode, an organic light emitting diode, or a micro light emitting diode. The light emitter 210 may include, for example, a pair of electrodes and a light emitting layer between the pair of electrodes. For example, the pair of electrodes may be a stretchable electrode, the light emitting layer may be a stretchable light emitting layer, and thus the light emitter 210 may be, for example, a stretchable element.

For example, one of the pair of electrodes may be a light-transmitting electrode and the other may be a reflecting electrode, for example, an electrode disposed close to the substrate 110 may be a light-transmitting electrode. For example, the pair of electrodes may be stretchable electrodes, and the stretchable electrodes may include, for example, a stretchable conductor, or may have a stretchable shape such as a wavy, wrinkled, pop-up, or non-planar mesh shape.

For example, the light emitting layer may include a light emitting material such as an organic light emitting material, a quantum dot, and/or perovskite, but is not limited thereto.

The organic light-emitting material may include, for example, perylene or a derivative thereof, rubrene or a derivative thereof, 4-(dicyanomethylene)-2-methyl-6-[p-(dimethylamino)styryl]-4H-pyran or a derivative thereof, cumarin or a derivative thereof, carbazole or a derivative thereof, an organometallic compound including Pt, Os, Ti, Zr, Hf, Eu, Tb, Tm, Rh, Ru, Re, Be, Mg, Al, Ca, Mn, Co, Cu, Zn, Ga, Ge, Pd, Ag and/or Au, or a combination thereof. The quantum dot may include, for example, a Group II-VI semiconductor compound, a Group III-V semiconductor compound, a Group IV-VI semiconductor compound, a Group IV semiconductor element or compound, a Group I-III-VI semiconductor compound, a Group I-II-IV-VI semiconductor compound, a Group II-III-V semiconductor compound, or a combination thereof. The Group II-VI semiconductor compound may be for example a binary element of CdSe, CdTe, ZnS, ZnSe, ZnTe, ZnO, HgS, HgSe, HgTe, MgSe, MgS, or a combination thereof; a ternary element of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, or a combination thereof; a quaternary element of ZnSeSTe, HgZnTeS, CdZnSeS, CdZnSeTe, CdZnSTe, CdHgSeS, CdHgSeTe, CdHgSTe, HgZnSeS, HgZnSeTe, HgZnSTe, or a combination thereof; or a combination thereof, but is not limited thereto. The Group III-V semiconductor compound may be for example a binary element of GaN, GaP, GaAs, GaSb, AlN, AlP, AlAs, AlSb, InN, InP, InAs, InSb, or a combination thereof; a ternary element of GaNP, GaNAs, GaNSb, GaPAs, GaPSb, AlNP, AlNAs, AlNSb, AlPAs, AlPSb, InNP, InNAs, InNSb, InPAs, InPSb, or a combination thereof; a quaternary element of GaAlNP, GaAlNAs, GaAlNSb, GaAlPAs, GaAlPSb, GaInNP, GaIn-NAs, GaInNSb, GaInPAs, GaInPSb, InAlNP, InAlNAs, InAlNSb, InAlPAs, InAlPSb, or a combination thereof; or a combination thereof, but is not limited thereto. The Group IV-VI semiconductor compound may be for example a binary element of SnS, SnSe, SnTe, PbS, PbSe, PbTe, or a combination thereof; a ternary element of SnSeS, SnSeTe, SnSTe, PbSeS, PbSeTe, PbSTe, SnPbS, SnPbSe, SnPbTe, or a combination thereof; a quaternary element of SnPbSSe, SnPbSeTe, SnPbSTe, or a combination thereof; or a combination thereof, but is not limited thereto. The Group IV semiconductor element or compound may be for example a singular element semiconductor of Si, Ge, or a combination thereof; a binary element semiconductor of SiC, SiGe, or a combination thereof; or a combination thereof, but is not limited thereto. The Group I-III-VI semiconductor compound may be for example selected from CuInSe$_2$, CuInS$_2$, CuInGaSe, CuInGaS, or a combination thereof, but is not limited thereto. The Group I-II-IV-VI semiconductor compound may be for example CuZnSnSe, CuZnSnS, or a combination thereof, but is not limited thereto. The Group II-III-V semiconductor compound may include for example InZnP, but is not limited thereto. The perovskite may include, for example, CH$_3$NH$_3$PbBr$_3$, CH$_3$NH$_3$PbI$_3$, CH$_3$NH$_3$SnBr$_3$, CH$_3$NH$_3$SnI$_3$, CH$_3$NH$_3$Sn$_{1-x}$Pb$_x$Br$_3$, CH$_3$NH$_3$Sn$_{1-x}$Pb$_x$I$_3$, HC(NH$_2$)$_2$PbI$_3$, HC(NH$_2$)$_2$SnI$_3$, (C$_4$H$_9$NH$_3$)$_2$PbBr$_4$, (C$_6$H$_5$CH$_2$NH$_3$)$_2$PbBr$_4$, $(C_6H_5CH_2NH_3)_2PbI_4$, $(C_6H_5C_2H_4NH_3)_2PbBr_4$, $(C_6H_{13}NH_3)_2(CH_3NH_3)_{n-1}PbnI_{3n+1}$, or a combination thereof, but is not limited thereto.

The emission spectrum of the light emitting layer may include at least a portion of light in a visible and/or infrared wavelength spectrum, for example, including at least a portion of the blue wavelength spectrum, the green wavelength spectrum, the red wavelength spectrum, and the (near) infrared wavelength spectrum.

The sensor 220 may be configured to absorb and detect (e.g., absorb and/or convert into an electric signal) light (e.g., light emitted by one or more of the light emitters 210) reflected by the internal tissue of the living body. Each sensor 220 includes a plurality of photo-detecting elements 220-1, 220-2, . . . , and 220-n for detecting light of different absorption spectrum. Herein, as an example, n plurality of photo-detecting elements 220-1, 220-2, . . . , 220-n are expressed, and n may be an integer of 2 or more, for example, 3 or more, and may be an integer of 5 or more, for example, 2 to 100, 3 to 100, or 5 to 100, but is not limited thereto. The plurality of photo-detecting elements 220-1, 220-2, . . . , and 220-n may be, for example, stacked in a thickness direction of the substrate 110. Photo-detecting elements 220-1, 220-2, . . . , and 220-n may be understood to be stacked on each other based on photo-detecting elements 220-1, 220-2, . . . , and 220-n extending in parallel in one or more directions (e.g., X and/or Y directions) and being arranged in a direction extending perpendicular to the direction(s) in which the photo-detecting elements 220-1, 220-2, . . . , and 220-n extend (e.g., a Z direction) such that the photo-detecting elements 220-1, 220-2, . . . , and 220-n overlap in the perpendicular direction.

Each of the photo-detecting elements 220-1, 220-2, . . . , and 220-n may be, for example, an inorganic or organic diode configured to absorb light having a different absorption spectrum $SP_{AB}$ in relation to each other. Each of the photo-detecting elements 220-1, 220-2, . . . , and 220-n may have wavelength selectivity, for example, selectively absorbing light in some wavelength spectrum of a visible wavelength spectrum and/or an infrared wavelength spectrum and for example, each independently may be configured to selectively absorb light of a particular (or, alternatively, predetermined) wavelength spectrum belonging to any one of a blue wavelength spectrum, a green wavelength spectrum, a red wavelength spectrum, or a (near) infrared wavelength spectrum. The photo-detecting elements 220-1, 220-2, . . . , and 220-n may have respective absorption peak wavelengths Amax that are within a visible wavelength spectrum or an infrared wavelength spectrum. An absorption peak wavelength Amax of the blue wavelength spectrum may fall within greater than or equal to about 400 nm and less than or equal to about 500 nm, an absorption peak wavelength Amax of the green wavelength spectrum may belong to about 500 nm to about 600 nm, an absorption peak wavelength Amax of the red wavelength spectrum may be greater than about 600 nm and less than or equal to about 700 nm, and an absorption peak wavelength Amax of the (near) infrared wavelength spectrum may be greater than about 700 nm and less than or equal to about 3000 nm. For example, each absorption peak wavelength Amax of the photo-detecting elements 220-1, 220-2, . . . , and 220-n may be within about 450 nm to about 1200 nm.

Referring to FIGS. 3A and 3B, when absorption peak wavelengths of the first photo-detecting element 220-1, the second photo-detecting element 220-2, and the $n^{th}$ photo-detecting element 220-n are $\lambda_1$, $\lambda d$, and $\lambda_n$, respectively, absorption peak wavelengths $\lambda_1$, $\lambda_2$, . . . , $\lambda_n$ of each of photo-detecting elements 220-1, 220-2, . . . , and 220-n may be different from each other. For example, each difference between the absorption peak wavelengths $\lambda_1$, $\lambda_2$, . . . , $\lambda_n$ of the plurality of photo-detecting elements 220-1, 220-2, . . . , and 220-n may be greater than or equal to about 5 nm, greater than or equal to about 10 nm, greater than or equal to about 15 nm, greater than or equal to about 20 nm, greater than or equal to about 30 nm, greater than or equal to about 40 nm, or greater than or equal to about 50 nm, within the range, about 5 nm to about 500 nm, about 10 nm to about 500 nm, about 15 nm to about 500 nm, about 20 nm to about 500 nm, about 30 nm to about 500 nm, about 40 nm to about 500 nm, about 50 nm to about 500 nm, about 5 nm to about 300 nm, about 10 nm to about 300 nm, about 15 nm to about 300 nm, about 20 nm to about 300 nm, about 30 nm to about 300 nm, about 40 nm to about 300 nm or about 50 nm to about 300 nm.

The absorption spectrum $SP_{AB}$ of each of photo-detecting elements 220-1, 220-2, . . . , and 220-n may belong to, for example, about 380 nm to about 2000 nm. Absorption peak wavelengths $\lambda_1$, $\lambda_2$, . . . , $\lambda_n$ of each of photo-detecting elements 220-1, 220-2, . . . , and 220-n may independently for example be about 450 nm to about 1200 nm, within the range, about 470 nm to about 1150 nm, about 480 nm to about 1100 nm, about 500 nm to about 1000 nm, about 550 nm to about 1000 nm, or about 600 nm to about 1000 nm.

In some example embodiments, since the light of the absorption spectrum detected by each of photo-detecting elements 220-1, 220-2, . . . , and 220-n is irradiated from the light emitter 210, an emission spectrum $SP_{EL}$ of the light emitter 210 may include wavelength spectra $SP_{AB}$ sensed by each of the photo-detecting elements 220-1, 220-2, . . . , and 220-n of the sensor 220, and may include, for example, all of the absorption peak wavelengths $\lambda_1$, $\lambda_2$, . . . , $\lambda_n$ of the plurality of photo-detecting elements 220-1, 220-2, . . . , 220-n may be included. For example, each emission spectrum $SP_{EL}$ of each light emitter 210 of the plurality of light emitters 210 may include the respective absorption peak wavelengths $\lambda_1$, $\lambda_2$, . . . , $\lambda_n$ (e.g., all of said absorption peak wavelengths) of the plurality of photo-detecting elements 220-1, 220-2, . . . , 220-n of the plurality of sensors 220. For example, the emission spectrum $SP_{EL}$ of the light emitter 210 may fall within about 380 nm to about 2000 nm, within the range about 380 nm to about 1800 nm, about 380 nm to about 1500 nm, about 400 nm to about 1400 nm, about 400 nm to about 1300 nm, about 400 nm to about 1200 nm, about 450 nm to about 1200 nm, about 470 nm to about 1150 nm, about 480 nm to about 1100 nm, about 500 nm to about 1000 nm, about 550 nm to about 1000 nm, or about 600 nm to about 1000 nm.

For example, each of photo-detecting elements 220-1, 220-2, . . . , and 220-n may be, for example, an organic or inorganic diode including a pair of electrodes and an absorption layer between the pair of electrodes. For example, one of the pair of electrodes in each of photo-detecting elements 220-1, 220-2, . . . , and 220-n may be a light-transmitting electrode and the other may be a reflecting electrode, for example, an electrode disposed close to the substrate 110 may be a light-transmitting electrode. For example, the pair of electrodes may be stretchable electrodes, and the stretchable electrodes may include, for example, a stretchable conductor, or may have a stretchable shape such as a wavy, wrinkled, pop-up, or non-planar mesh shape.

For example, the absorption layer included in each of the photo-detecting elements 220-1, 220-2, . . . , and 220-n may be a photoelectric conversion layer configured to absorb light of a particular (or, alternatively, predetermined) absorption spectrum and convert the absorbed light into an electrical signal. The absorption layer included in each of the photo-detecting elements 220-1, 220-2, . . . , and 220-$n$ may include, for example, an inorganic absorbing semiconductor, an organic absorbing semiconductor, and/or an organic/inorganic absorbing semiconductor. For example, the inorganic absorbing semiconductor, the organic absorbing semiconductor, and/or the organic-inorganic light absorbing semiconductor may be a p-type semiconductor or an n-type semiconductor forming a pn junction. The absorption layer included in each of the photo-detecting elements 220-1, 220-2, . . . , and 220-$n$ may be configured to absorb a part of light in the visible wavelength spectrum and/or the infrared wavelength spectrum, respectively. For example, the absorption layer may be configured to absorb light in the absorption spectrum having absorption peak wavelengths $\lambda_1$, $\lambda_2$, . . . , $\lambda_n$. For example, the absorption layer may be a stretchable light absorption layer. Each of the photo-detecting elements 220-1, 220-2, . . . , and 220-$n$ may be, for example, a stretchable element.

Light absorbed and detected by the photo-detecting elements 220-1, 220-2, . . . , and 220-$n$ may be light reflected by internal tissues of the living body. By analyzing the electrical signal that is selectively absorbed and photoelectrically converted by each photo-detecting element 220-1, 220-2, . . . , and 220-$n$ having wavelength selectivity, an image according to a depth of the internal tissue of the living body (e.g., a "depth image" as described herein) may be confirmed and from this, spatial information on the internal tissues of the living body may be obtained. These are described later. In some example embodiments, substrate 110 may be absent from the bio imaging system 100. For example, the bio imaging system 100 may include the light emitter-sensor array 200 on or within a non-stretchable (e.g., rigid) substrate, but example embodiments are not limited thereto.

As an example, a sensor 220 having a structure in which two photo-detecting elements 220-1 and 220-2 are stacked will be described.

Figure 4:
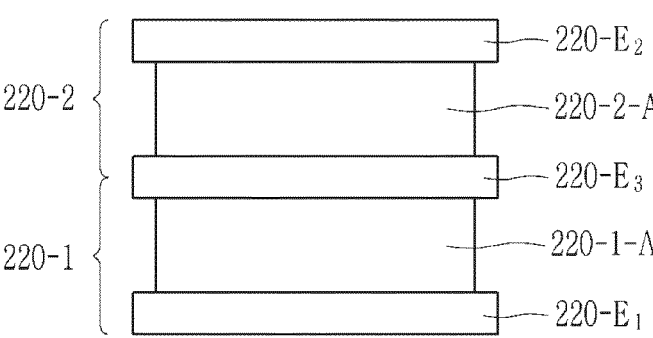
FIG. 4 is a cross-sectional view showing a sensor according to an example.
Figure 5A:
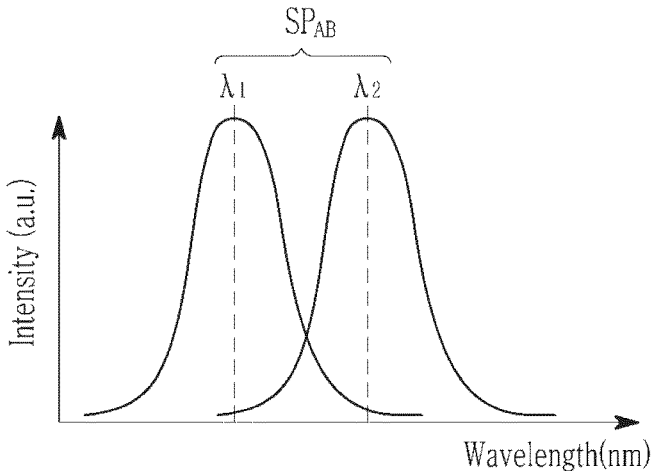
FIGS. 5A and 5B are graphs showing examples of an emission spectrum of a light emitter and an absorption spectrum of a sensor in a bio imaging system including the sensor of FIG. 4.
Figure 5B:
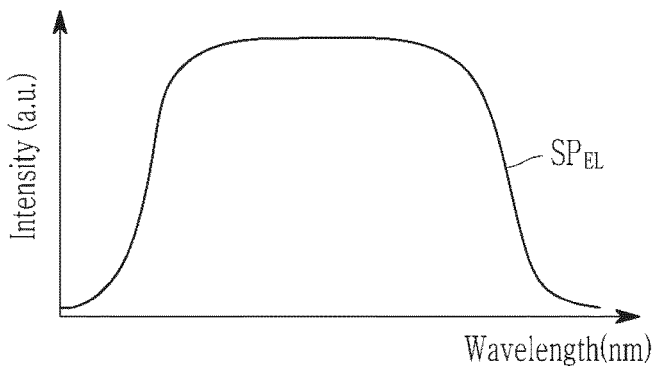

FIG. 4 is a cross-sectional view showing a sensor according to an example, and FIGS. 5A and 5B are graphs showing examples of an emission spectrum of a light emitter and an absorption spectrum of a sensor in a bio imaging system including the sensor of FIG. 4.

The sensor 220 according to an example includes a first photo-detecting element 220-1 and a second photo-detecting element 220-2 that are stacked on (e.g., directly on) each other. The first photo-detecting element 220-1 includes a first absorption layer 220-1-A configured to selectively absorb light in an absorption spectrum having a first absorption peak wavelength $\lambda_1$, and the second photo-detecting element 220-2 includes a second absorption layer 220-2-A configured to selectively absorb light in an absorption spectrum having a second absorption peak wavelength $\lambda_2$. Wavelength spectra of the first absorption layer 220-1-A and the second absorption layer 220-2-A may each independently have wavelength selectivity. The first absorption peak wavelength $\lambda_1$ and the second absorption peak wavelength $\lambda_2$ may each independently belong to any one of a blue wavelength spectrum, a green wavelength spectrum, a red wavelength spectrum, or an (near) infrared wavelength spectrum. The second absorption peak wavelength $\lambda_2$ may be longer than the first absorption peak wavelength $\lambda_1$. A difference between the first absorption peak wavelength $\lambda_1$ and the second absorption peak wavelength $\lambda_2$ may be, for example, may be greater than or equal to about 5 nm, greater than or equal to about 10 nm, greater than or equal to about 15 nm, greater than or equal to about 20 nm, greater than or equal to about 30 nm, greater than or equal to about 40 nm, or greater than or equal to about 50 nm.

The first photo-detecting element 220-1 includes a pair of electrodes 220-$E_1$ and 220-$E_3$ facing each other in the center of the first absorption layer 220-1-A, and the second photo-detecting element 220-2 includes a pair of electrodes 220-$E_2$ and 220-$E_3$ facing each other in the center of the second absorption layer 220-2-A. For example, one of the electrodes 220-$E_1$ or 220-$E_3$ may be an anode and the other may be a cathode. For example, one of the electrodes 220-$E_2$ or 220-$E_3$ may be a cathode and the other may be an anode. The electrode 220-$E_3$ between the first absorption layer 220-1-A and the second absorption layer 220-2-A may be a common electrode of the first photo-detecting element 220-1 and the second photo-detecting element 220-2. Accordingly, each sensor 220 may include a first electrode (e.g., electrode 220-$E_1$) on one surface of the first absorption layer 220-1-A, a second electrode (e.g., electrode 220-$E_2$) on one surface of the second absorption layer 220-2-A, and a third electrode facing the first electrode and the second electrode (e.g., electrode 220-$E_3$) and between the first absorption layer 220-1-A and the second absorption layer 220-2-A, where the third electrode is a common electrode of the first photo-detecting element 220-1 and the second photo-detecting element 220-2. However, the present disclosure is not limited thereto, and the electrode 220-$E_3$ between the first absorption layer 220-1-A and the second absorption layer 220-2-A may be an individual electrode of the first photo-detecting element 220-1 and the second photo-detecting element 220-2.

The emission spectrum SPEC of the light emitter 210 may include an absorption spectrum $SP_{AB}$ absorbed and detected by the first and second photo-detecting elements 220-1 and 220-2 of the sensor 220, for example all of the absorption peak wavelengths $\lambda_1$ and $\lambda_2$ of the first and second photo-detecting elements 220-1 and 220-2 may be included.

As an example, an example of the sensor 220 having a structure in which three photo-detecting elements 220-1, 220-2, and 220-3 are stacked will be described.

Figure 6:
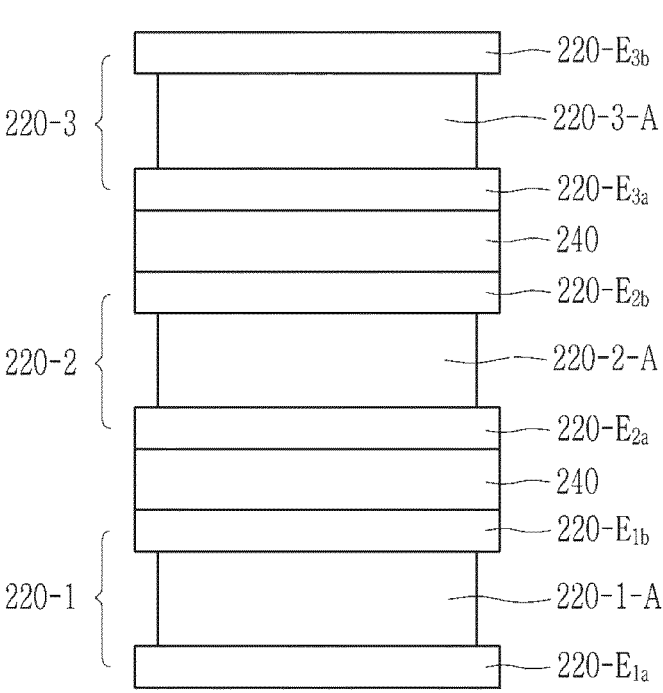
FIG. 6 is a cross-sectional view showing a sensor according to an example.
Figure 7A:
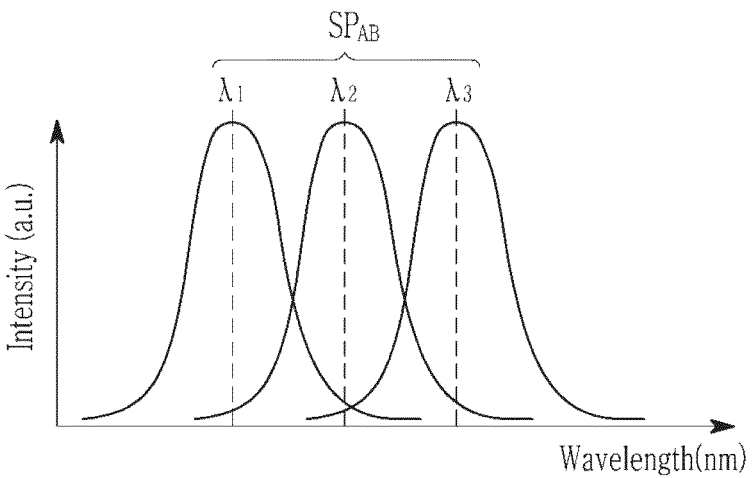
FIGS. 7A and 7B are graphs showing an example of wavelength spectra of a light emitter and the sensor of the bio imaging system including the sensor of FIG. 6.
Figure 7B:
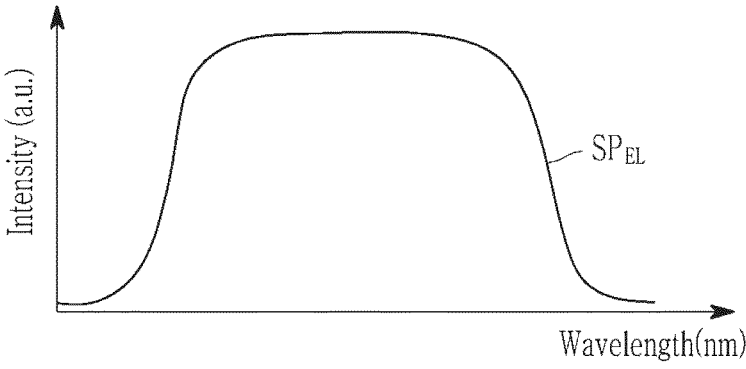

FIG. 6 is a cross-sectional view showing a sensor according to an example, and FIGS. 7A and 7B are graphs showing an example of wavelength spectra of a light emitter and the sensor of the bio imaging system including the sensor of FIG. 6.

The sensor 220 according to an example includes the first photo-detecting element 220-1, the second photo-detecting element 220-2, and the third photo-detecting element 220-3, which are stacked on one another. The first photo-detecting element 220-1 includes the first absorption layer 220-1-A configured to selectively absorb light of an absorption spectrum having the first absorption peak wavelength $\lambda_1$, the second photo-detecting element 220-2 includes the second absorption layer 220-2-A configured to selectively absorb light of an absorption spectrum having the second absorption peak wavelength $\lambda_2$ differing from that of the first absorption peak wavelength $\lambda_1$, and a third photo-detecting element 220-3 includes a third absorption layer 220-3-A configured to selectively absorb light of an absorption spectrum having a third absorption peak wavelength $\lambda_3$ differing from those of the first and second absorption peak wavelengths $\lambda_1$ and $\lambda_2$. For example, the third absorption peak wavelength $\lambda_3$ may be longer than the second absorption peak wavelength $\lambda_2$.

The wavelength spectra of the first absorption layer 220-1-A, the second absorption layer 220-2-A, and the third absorption layer 220-3-A may differ one another, and the first absorption peak wavelength $\lambda_1$, the second absorption peak wavelength $\lambda_2$, and the third absorption peak wavelength $\lambda_3$ may independently belong to one of a blue wavelength spectrum, a green wavelength spectrum, a red wavelength spectrum, or a (near) infrared wavelength spectrum and independently have a difference of for example, greater than or equal to about 5 nm, greater than or equal to about 10 nm, greater than or equal to about 15 nm, greater than or equal to about 20 nm, greater than or equal to about 30 nm, greater than or equal to about 40 nm, or greater than or equal to about 50 nm.

The first photo-detecting element 220-1 may include a pair of electrodes 220-E$_{1a}$ and 220-E$_{1b}$ facing each other and the first absorption layer 220-1-A as the center, wherein either one of the pair of electrodes 220-E$_{1a}$ or 220-E$_{1b}$ may be, for example, an anode, while the other may be a cathode. The second photo-detecting element 220-2 may include a pair of electrodes 220-E$_{2a}$ and 220-E$_{2b}$ facing each other in the center of the second absorption layer 220-2-A, wherein either one of the pair of electrodes 220-E$_{2a}$ or 220-E$_{2b}$ may be for example, an anode, while the other may be a cathode. The third photo-detecting element 220-3 may include a pair of electrodes 220-E$_{3a}$ and 220-E$_{3b}$ facing each other in the center of the third absorption layer 220-3-A, wherein either one of the pair of electrodes 220-E$_{3a}$ or 220-E$_{3b}$ may be, for example, an anode, while the other may be a cathode. For example, when the substrate 110 is disposed at the side of the first photo-detecting element 220-1, the electrode 220-E$_{3b}$ disposed farthest from the substrate 110 may be a reflecting electrode, and the other electrodes 220-E$_{1a}$, 220-E$_{1b}$, 220-E$_{2a}$, 220-E$_{2b}$, and 220-E$_{3a}$ may be light-transmitting electrodes. Insulating layers 240 may be disposed between the first photo-detecting element 220-1 and the second photo-detecting element 220-2 and between the second photo-detecting element 220-2 and the third photo-detecting element 220-3, respectively.

An emission spectrum SPEC of the light emitter 210 may include wavelength spectra $SP_{AB}$ sensed in the first, second, and third photo-detecting elements 220-1, 220-2, and 220-3 of the sensor 220, for example, all the absorption peak wavelengths $\lambda_1$, $\lambda_2$, and $\lambda_3$ of the first, second, and third photo-detecting elements 220-1, 220-2, and 220-3.

In the bio imaging system 100 according to some example embodiments, the sensor 220 including the plurality of photo-detecting elements 220-1, 220-2, . . . , and 220-$n$ may secure a plurality of images along a depth direction from the skin surface by using that a penetration depth of light differs depending on a wavelength. These plural images may be combined to obtain information such as a location, shape, size, and/or thickness of the internal tissues of the living body, and this information may be used to obtain spatial information of the internal tissues of the living body. In addition, this spatial information may be separated and/or extracted to effectively obtain information of the internal tissues of the living body present at a particular depth from the skin surface.

Specifically, when the skin is irradiated with light, the penetration depth of the light from the skin surface is different depending on a wavelength, and in general, light of a long wavelength spectrum may penetrate relatively deeper than light of a short wavelength spectrum. In some example embodiments, since the light of the long wavelength spectrum may also be scattered, while it pass several tissues along the depth direction from the skin surface, information obtained from light of a particular (or, alternatively, predetermined) wavelength may not images of the internal tissues present at the maximum penetration depth but images of all the internal tissues of the living body within a penetration depth of the light. Accordingly, it may be difficult to selectively obtain clear images of the internal tissues of the living body such as blood vessels located at a particular depth from the surface of the skin. Such images of internal tissues of the living body at a particular depth from the surface of the skin of the living body may be referred to herein as "depth images."

In some example embodiments, the light emitter 210 configured to radiate light of a wide absorption spectrum and the sensor 220 including the plurality of photo-detecting elements 220-1, 220-2, . . . , and 220-$n$ having wavelength selectivity may be aligned as an array to combine different image information obtained from the plurality of photo-detecting elements 220-1, 220-2, . . . , and 220-$n$ depending on a light penetration depth and then, separate and/or extract image information of the internal tissues of the living body along the depth direction from the skin surface and thus obtain information of the internal tissues of the living body present at a particular depth.

For example, in the sensor 220 having a stacking structure of two photo-detecting elements 220-1 and 220-2 shown in FIGS. 4 and 5, when the first photo-detecting element 220-1 may be configured to sense light of the first absorption spectrum having the first absorption peak wavelength $\lambda_1$, which is a relatively short wavelength, while the second photo-detecting element 220-2 may be configured to sense light of the second wavelength spectrum having the second absorption peak wavelength $\lambda_2$, which is a relatively long wavelength, the light of the first and second wavelength spectra radiated from the light emitter 210 respectively may penetrate the skin and reach each maximum depth from the skin surface and then may be reflected, and this reflected light may be respectively absorbed and sensed in the first and second photo-detecting elements 220-1 and 220-2 depending on a wavelength. Herein, even if the light of the first and second wavelength spectra from the skin surface has any penetration depth distribution, an image obtained from the second photo-detecting element 220-2 sensing light of a relatively long wavelength spectrum (e.g., a second image) may be relatively deeper from an image obtained from the first photo-detecting element 220-1 sensing light of a relatively short wavelength spectrum, and a difference between the image obtained from the second photo-detecting element 220-2 (e.g., second image) sensing light of a relatively long wavelength spectrum and the image obtained from the first photo-detecting element 220-1 (e.g., first image) sensing light of a relatively short wavelength spectrum may be extracted to obtain image information at a depth where the light of the second absorption spectrum alone penetrates (e.g., a first depth image). Accordingly, image information of the internal tissues of the living body at a particular depth may be effectively obtained.

Likewise, for example, in the sensor 220 including three photo-detecting elements 220-1, 220-2, and 220-3 shown in FIGS. 6 and 7, when the first photo-detecting element 220-1 may be configured to sense light of the first absorption spectrum having the first absorption peak wavelength $\lambda_1$, which is the shortest wavelength, the third photo-detecting element 220-3 may be configured to sense light of the third absorption spectrum having the third absorption peak wavelength $\lambda_3$, which is relatively the longest wavelength, and the second photo-detecting element 220-2 may be configured to sense light of the second absorption spectrum having the second absorption peak wavelength $\lambda_2$ between the first absorption peak wavelength $\lambda_1$ and the third absorption peak wavelength $\lambda_3$, the light of the first, second, and third wavelength spectra out of the light radiated from the light emitter 210 has each penetration depth from the skin surface, and the light of the first, second, and third wavelength spectra independently may pass the skin and then, may be transmitted up to each maximum penetration depth but reflected by the internal tissues of the living body, and the reflected light may be absorbed and sensed in the first, second, and third photo-detecting elements 220-1, 220-2, and 220-3 depending on a wavelength. Herein, even though the light of the first, second, and third wavelength spectra from the skin surface has any penetration depth distribution, an image obtain from the third photo-detecting element 220-3 configured to sense light of a relatively longer absorption spectrum (e.g., a third image) may be deeper than an image from the second photo-detecting element 220-2 configured to sense light of a relatively short absorption spectrum (e.g., a second image), and the image obtained from the second photo-detecting element 220-2 configured to sense light of the relatively long absorption spectrum may be deeper than the image obtained from the first photo-detecting element 220-1 configured to sense the light of the relatively short absorption spectrum (e.g., a first image).

Accordingly, differences of the images from the third photo-detecting element 220-3 and the second photo-detecting element 220-2 (e.g., a second difference between the third and second images) are separated and/or extracted to obtain image information (e.g., a second depth image) at a depth where the light of the third absorption spectrum alone penetrate (e.g., a second depth), and likewise, differences of the images from the second photo-detecting element 220-2 and the first photo-detecting element 220-1 (e.g., a first difference between the first and second images) are separated and/or extracted to secure image information (e.g., a first depth image) at a depth where the light of the second absorption spectrum alone penetrates (e.g., a first depth, where the second depth is deeper than the first depth). Accordingly, image information of the internal tissues of the living body from the skin surface may be effectively obtained at a particular depth, and a plurality of "depth images" of the internal tissue of the living body according to depth from the surface of the skin may be obtained.

In this method, in the sensor 220 including n photo-detecting elements 220-1, 220-2, . . . , and 220-n, image differences of any two photo-detecting elements selected from the n photo-detecting elements 220-1, 220-2, . . . , and 220-n are separated and/or extracted and then, combined to obtain spatial information in a depth direction. The more the photo-detecting elements are, the more precise spatial information in the depth direction may be secured.

The bio imaging method of using the aforementioned bio imaging system 100 may include fixing (e.g., affixing, placing in direct contact, etc.) the bio imaging system 100 on the skin S; turning on (e.g., activating) some or all of the plurality of light emitters 210 to irradiate light to the skin S; selectively sensing (e.g., absorbing and/or converting into an electric signal) light that is the irradiated light that is scattered or reflected by the internal tissue of the living body through the skin S in each of a plurality of photo-detecting elements 220-1, 220-2, . . . , and 220-n of one or more sensors 220 of the bio imaging system 100 according to the wavelength spectrum of the light scattered and reflected to obtain (e.g., generate) a plurality of images; separating and/or extracting differences between the plurality of images of the internal tissues of the living body such as the blood vessel (BV) depending on a depth from the surface of the skin (S) to obtain a plurality of images according to depth from the surface of the skin (e.g., "depth images"); and combining the plurality of images (e.g., "depth images") of the internal tissues of the living body such as the blood vessel (BV) to obtain (e.g., generate) a three-dimensional image of the internal tissues of the living body.

An example of a method of obtaining image information of an internal tissue of the living body using the aforementioned bio imaging system will be described with reference to FIGS. 8 and 9.

Figure 8:
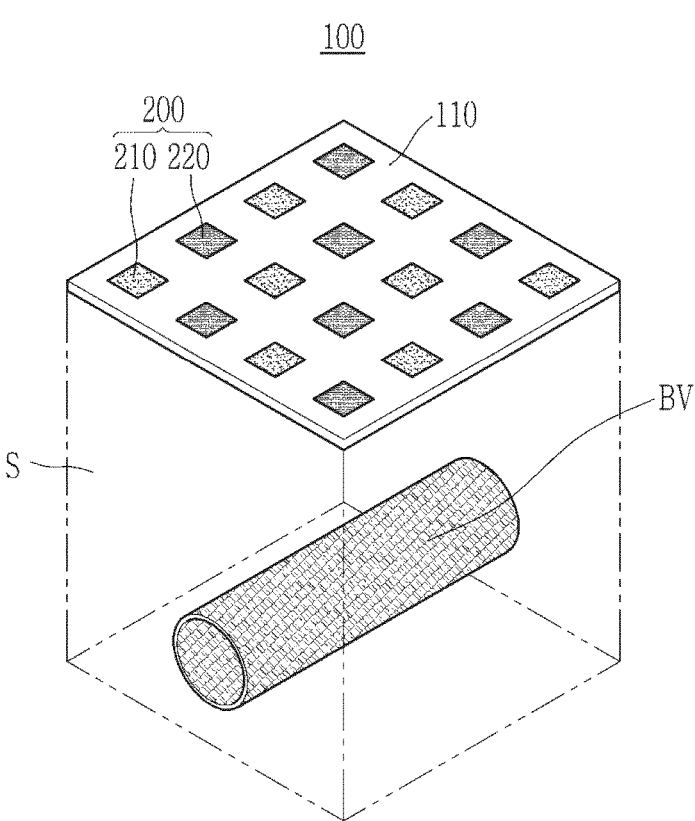
FIG. 8 is a schematic view schematically showing an example of a method of obtaining image information of internal tissue of the living body using a bio imaging system according to some example embodiments.
Figure 9:
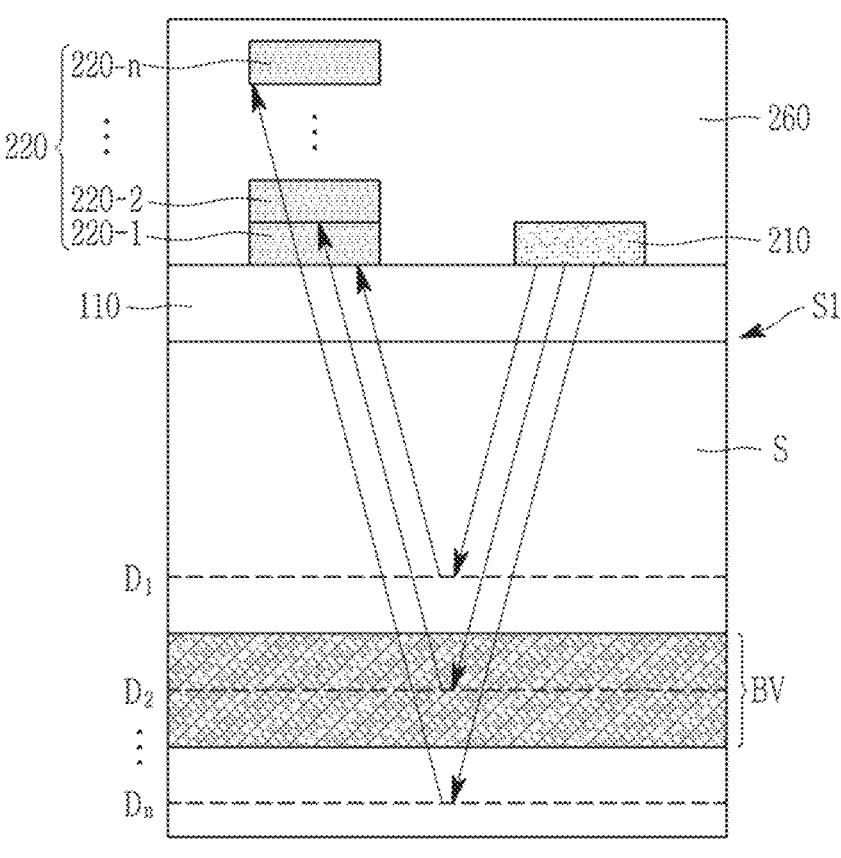
FIG. 9 is a cross-sectional view schematically showing an example of a method of obtaining image information of internal tissue of the living body using the bio imaging system of FIG. 8.

FIG. 8 is a schematic view schematically showing an example of a method of obtaining image information of internal tissue of the living body using a bio imaging system according to some example embodiments, and FIG. 9 is a cross-sectional view schematically showing an example of a method of obtaining image information of internal tissue of the living body using the bio imaging system of FIG. 8.

As described above, when the plurality of light emitters 210 of the bio imaging system 100 is turned on to radiate light into the skin S, the light may penetrate different depths from the skin surface S1 depending on a wavelength spectrum of the radiated light, and light of a relatively long wavelength may penetrate deeper than light of a relatively short wavelength.

Accordingly, referring to FIG. 9, penetrable depths $D_1$, $D_2$, . . . , $D_n$ of the light radiated from the plurality of light emitters 210 have a particular (or, alternatively, predetermined) distribution depending on a wavelength, and images reflected by the internal tissues of the living body at different depths depending on a wavelength may be selectively obtained by the plurality of photo-detecting elements 220-1, 220-2, . . . 220-n configured to selectively absorb light of different wavelength spectra from each other. For example, when the first photo-detecting element 220-1 among the plurality of photo-detecting elements 220-1, 220-2, . . . , and 220-n may be configured to absorb light of the first absorption spectrum, which is the shortest wavelength spectrum, and the $n^{th}$ photo-detecting element 220-n may be configured to absorb light of the $n^{th}$ absorption spectrum, which is relatively the longest wavelength spectrum, signals obtained from the light of the first to $n^{th}$ wavelength spectra may respectively provide images from the relatively nearest depth D1 to the deepest depth $D_n$ from the skin surface S1, and based on these images, image differences according to each depth are separated and extracted to identify the lowest, middle, and highest points of the blood vessel BV and thus obtain a three-dimensional image of the blood vessel BV. This three-dimensional image of the blood vessel BV may be used to identify spatial information such as the location, shape, size, and/or thickness of blood vessel BV.

Another example of a method of obtaining image information of an internal tissue of the living body using the aforementioned bio imaging system will be described with reference to FIGS. 10 and 11.

Figure 10:
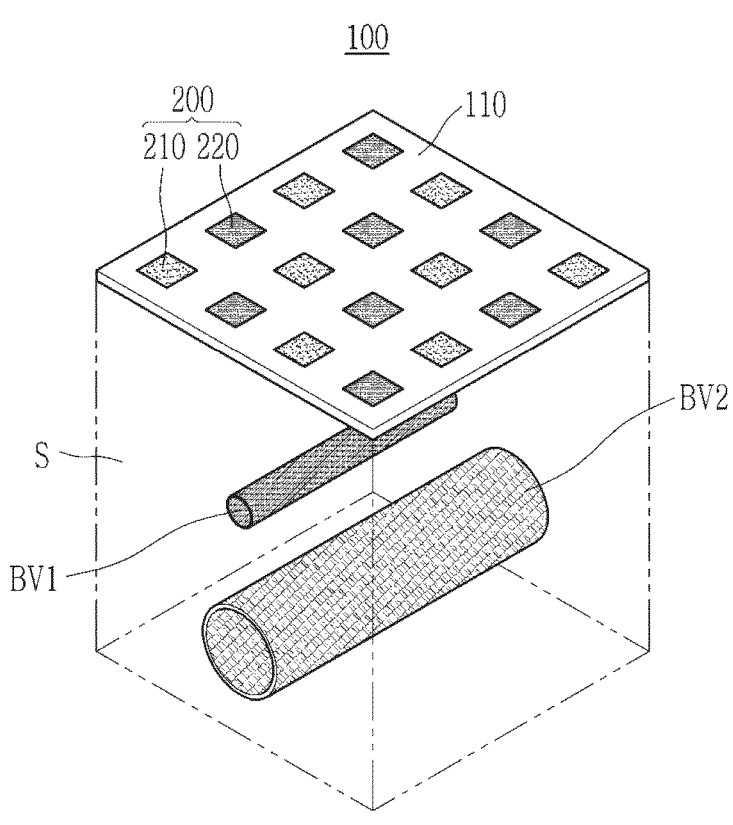
FIG. 10 is a schematic view schematically showing another example of a method of obtaining image information of internal tissue of the living body using a bio imaging system according to some example embodiments.
Figure 11:
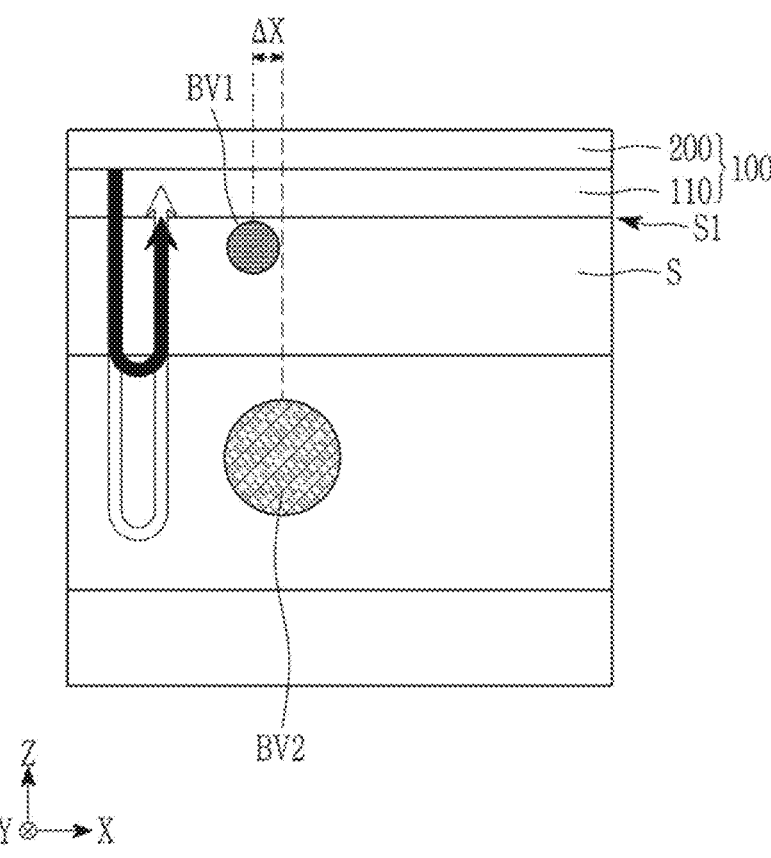
FIG. 11 is a cross-sectional view schematically showing another example of a method of obtaining image information of internal tissue of the living body using the bio imaging system of FIG. 10.

FIG. 10 is a schematic view schematically showing another example of a method of obtaining image information of internal tissue of the living body using a bio imaging system according to some example embodiments, and FIG. 11 is a cross-sectional view schematically showing another example of a method of obtaining image information of internal tissue of the living body using the bio imaging system of FIG. 10.

In the present example, when two blood vessels BV1 and BV2 are located in the depth direction, images of the two blood vessels BV1 and BV2 are separated and/or extracted to obtain an image of the blood vessels BV1 and BV2 at a particular depth.

In other words, as described above, the penetrable depths $D_1$, $D_2$, . . . , $D_n$ of light radiated from the light emitter 210 have a particular (or, alternatively, predetermined) distribution depending on a wavelength, information of the blood vessels BV1 and BV2 reflected at different depths depending on a wavelength may be selectively obtained from the plurality of photo-detecting elements 220-1, 220-2, . . . , and 220-n configured to absorb light of different wavelength spectra, and image information obtained from the light of the first to n$^{th}$ wavelength spectra may include spatial information from the relatively near depth $D_1$ to the deepest depth $D_n$ from the skin surface S1, differences of the plurality of images may not only be separated and/or extracted to identify the lowest, middle, and highest points of the blood vessels BV1 and BV2 and thus obtain each 3-dimensional images of the blood vessels BV1 and BV2, but also image differences of the blood vessels BV1 and BV2 may be extracted to obtain a clear image of the blood vessel BV2 without deteriorating resolution by the blood vessel BV1. Accordingly, when the plurality of blood vessels are located in the depth direction from the skin surface, spatial information of the internal tissues of the living body may be effectively identified in this way. Herein, an example of two blood vessels BV1 and BV2 located in the depth direction is illustrated, but other examples of n blood vessels in the depth direction may be illustrated in the same way.

Hereinafter, a bio imaging system according to some example embodiments is described.

Figure 12:
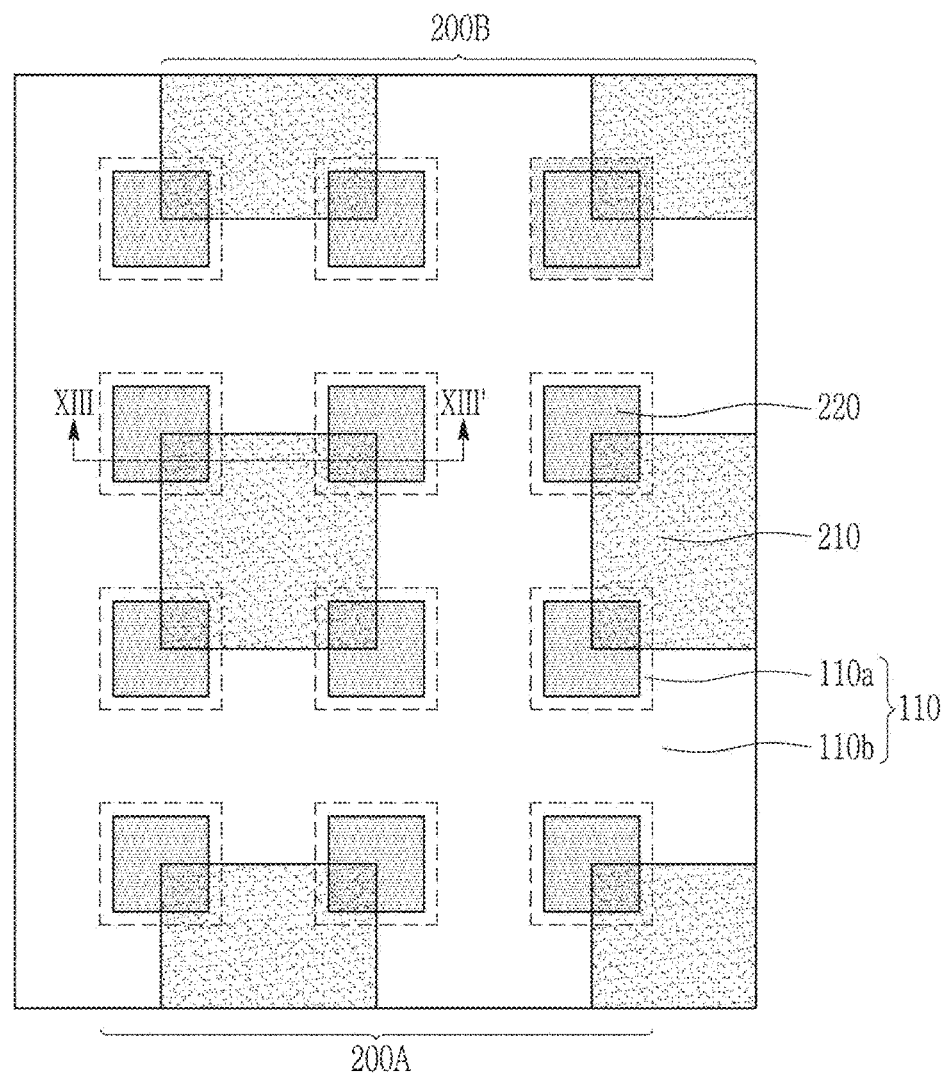
FIG. 12 is a plan view showing an example of a bio imaging system according to some example embodiments.
Figure 13:
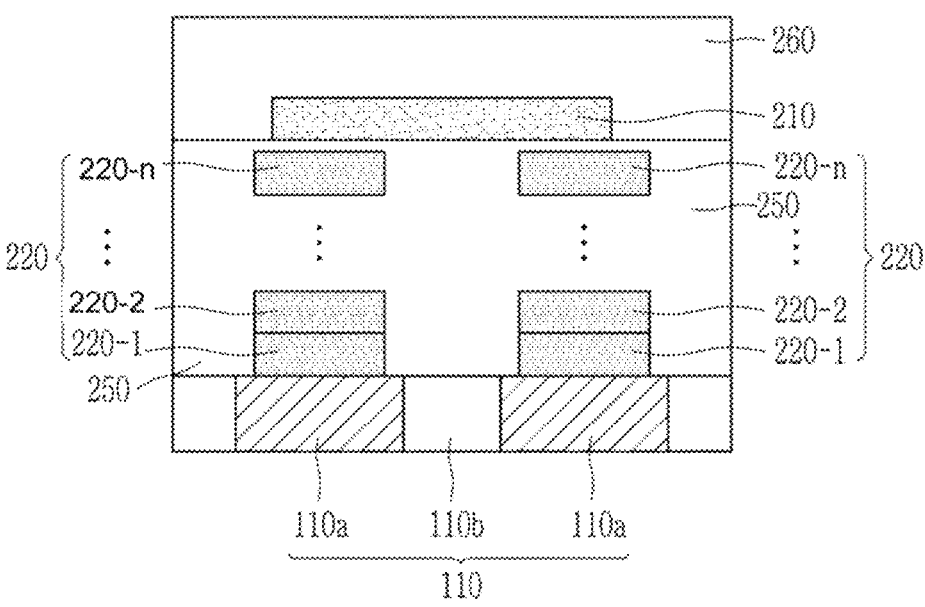
FIG. 13 is a cross-sectional view of an example of the bio imaging system of FIG. 12 taken along line XIII-XIII'.

FIG. 12 is a plan view showing an example of a bio imaging system according to some example embodiments, and FIG. 13 is a cross-sectional view of an example of the bio imaging system of FIG. 12 taken along line XIII-XIII'.

Referring to FIGS. 12 and 13, the bio imaging system 100 according to some example embodiments includes the substrate 110; a plurality of light emitters 210 and a plurality of sensors 220 on the substrate 110; and optionally an encapsulation film 260 covering the plurality of light emitters 210 and the plurality of sensors 220, like some example embodiments, including the example embodiments of FIGS. 1-11.

However, in the bio imaging system 100 of some example embodiments, including the example embodiments of FIGS. 12-13, unlike some example embodiments, including the example embodiments of FIGS. 1-11, the plurality of light emitters 210 and the plurality of sensors 220 are disposed at different depths from the substrate 110. In other words, the plurality of sensors 220 disposed at a first height from the substrate 110 may be, for example, arranged along a row and/or a column to form a sensor array 200A, and the plurality of light emitters 210 disposed at a second height from the substrate 110 may be, for example, arranged along a row and/or a column to form a light emitter array 200B. Accordingly, the light emitter array 200B and the sensor array 200A may be at different heights from the substrate 110. For example, the second height may be higher than that of the first height. Between the sensor array 200A and the light emitter array 200B, a transparent layer 250 may be included, which is a stretched transparent layer.

Figure 14:
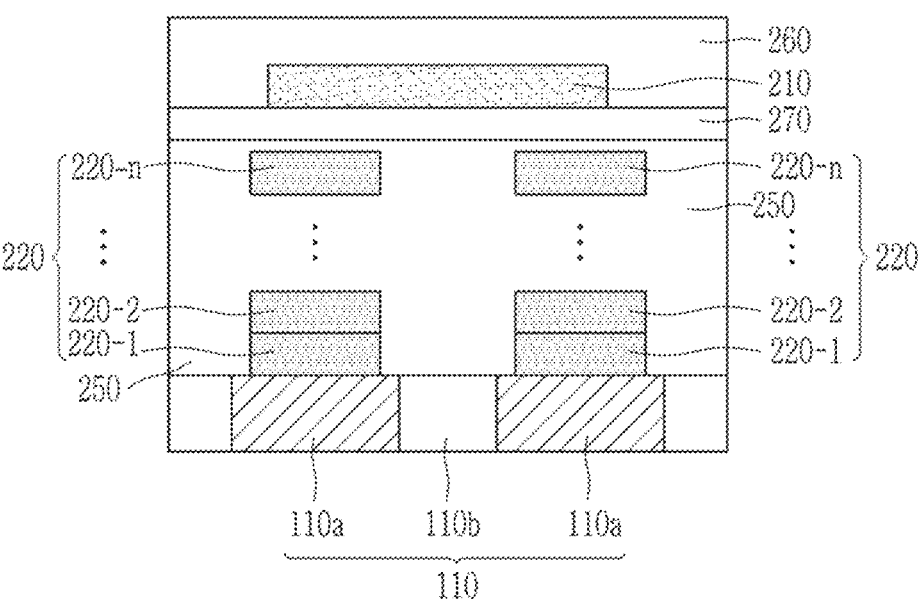
FIG. 14 is a cross-sectional view of another example of the bio imaging system of FIG. 12 taken along line XIII-XIII'.

FIG. 14 is a cross-sectional view of another example of the bio imaging system of FIG. 12 taken along line XIII-XIII'.

Referring to FIG. 14, the bio imaging system 100 of the some example embodiments, like some example embodiments, including the example embodiments of FIGS. 12-13, includes the substrate 110; the sensor array 200A on the substrate 110; the light emitter array 200B on the sensor array 200A; the transparent layer 250 between the sensor array 200A and the light emitter array 200B; and optionally the encapsulation film 260.

However, the bio imaging system 100 according to some example embodiments, including the example embodiments of FIG. 14, unlike some example embodiments, including the example embodiments of FIGS. 12-13, further includes a light diffusion layer 270 under the light emitter array 200B, and thus between the light emitter array 200B and the sensor array 200A. The light diffusion layer 270 may be between the substrate 110 and the light emitter array 200B, for example, on whole surface of the substrate 110. The light diffusion layer 270 may be configured to scatter and diffuse light radiated from the light emitter array 200B and evenly supply the light to the skin.

The bio imaging system 100 may be applied to a medical or security imaging device for identifying spatial information of the internal tissues of the living body, and this spatial information may be obtained temporarily or in real time. For example, the internal tissues of the living body may be blood vessels, and the spatial information such as a location, shape, size and/or thickness of the blood vessels may be used to predict or treat vascular diseases in advance.

The bio imaging system 100 may be, for example, a wearable bio imaging system or a skin-attached bio imaging system directly attached to the skin, and the skin-attached bio imaging system may be, for example, a patch-type bio imaging system or a band-type bio imaging system.

The bio imaging system 100 may further include a driving unit (e.g., processing circuitry) such as an integrated circuit (IC) and a processor (e.g., a central processing unit (CPU)) for obtaining an electrical signal as described above and separating and/or extracting spatial information of an internal tissue of the living body according to the electrical signal.

The bio imaging system 100 may further include a display unit, or display panel, (e.g., light emitting diode (LED) screen) for displaying images and spatial information of the internal tissue of the living body as various characters and/or images.

Hereinafter, some example embodiments are illustrated in more detail with reference to examples. However, the present scope of the example embodiments is not limited to the examples.

Optical Simulation I

Example 1

Blood vessel images are evaluated using a bio imaging system.

Figure 15:
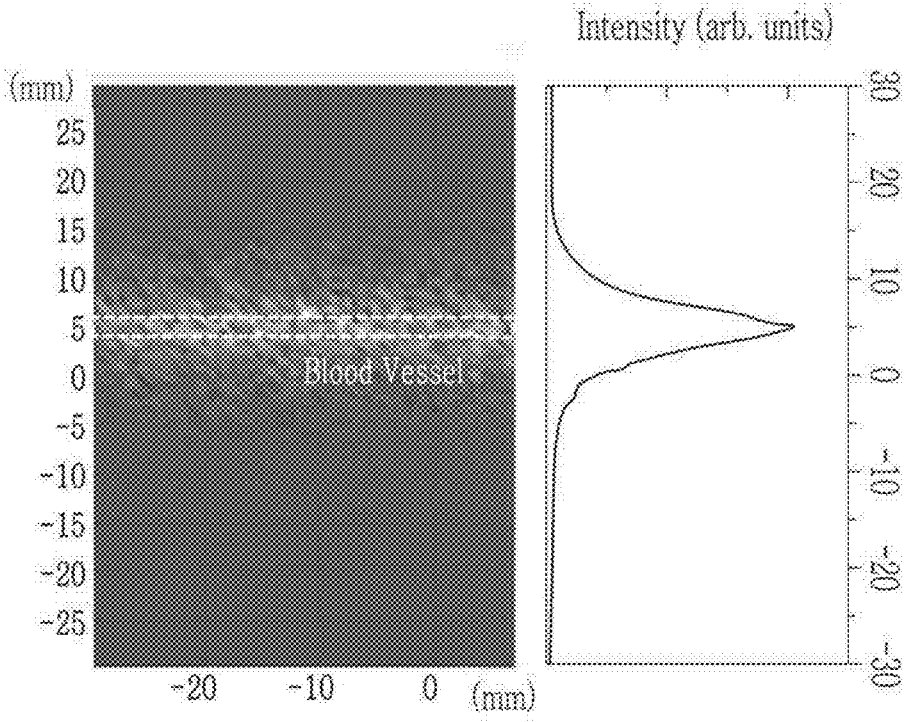
FIG. 15 is a graph showing a blood vessel image and spatial distribution obtained according to Example 1.

Simulation conditions are as follows:

Light emitter-sensor array shown in FIGS. 1 and 2
Stretchable substrate thickness: 0.02 mm
Blood vessel distribution in FIGS. 8 and 9
Light emitter: Surface light emitter (Plane light emitter, Lambertian)
Emission spectrum of light emitter: single wavelength of 650 nm
Upper electrode/lower electrode of light emitter: reflecting electrode/light-transmitting electrode
Absorption peak wavelength of photo-detecting element: single wavelength of 650 nm
Number of stacked photo-detecting elements: 1
Skin composition: skin thickness of 1.5 mm, fat thickness of 3 mm, muscle thickness of 30 mm, and
Internal quantum efficiency of the photo-detecting element is assumed to be 100%.
The results are shown in FIG. 15.
FIG. 15 is a graph showing a blood vessel image and spatial distribution obtained according to Example 1.

Referring to FIG. 15, the blood vessel image and the spatial distribution of blood vessel may be examined through the bio imaging system according to Example 1.

Optical Simulation II

Example 2

Each blood vessel image is evaluated when a plurality of blood vessels are distributed along a depth direction using a bio imaging system.

Simulation conditions are as follows:

Light emitter-sensor array shown in FIGS. 1 and 2

Stretchable substrate thickness: 0.02 mm

Blood vessel distribution in FIGS. 10 and 11

Light emitter: Surface light emitter (Plane light emitter, Lambertian)

Emission spectrum of light emitter: 650 nm to 710 nm

Upper electrode/lower electrode of light emitter: reflecting electrode/light-transmitting electrode Number of stacked photo-detecting elements: 2 (lower, upper)

Absorption peak wavelength of lower photo-detecting element: 650 nm

Upper electrode/lower electrode of lower photo-detecting element: light-transmitting electrode/light-transmitting electrode Absorption peak wavelength of upper photo-detecting element: 710 nm Upper electrode/lower electrode of upper photo-detecting element: reflecting electrode/light-transmitting electrode Internal quantum efficiency of the lower and upper photo-detecting elements is assumed to be 100%

Skin composition: skin thickness of 1.5 mm, fat thickness of 3 mm, muscle thickness of 30 mm, Information of upper blood vessel BV1: $x=0$ mm (ref.), $z=1.5$ mm (depth from skin surface), radius of 0.5 mm, and Information of lower blood vessel BV2: $x=3$ mm, $z=4$ mm (depth from skin surface), radius of 1.0 mm.

Figure 16:
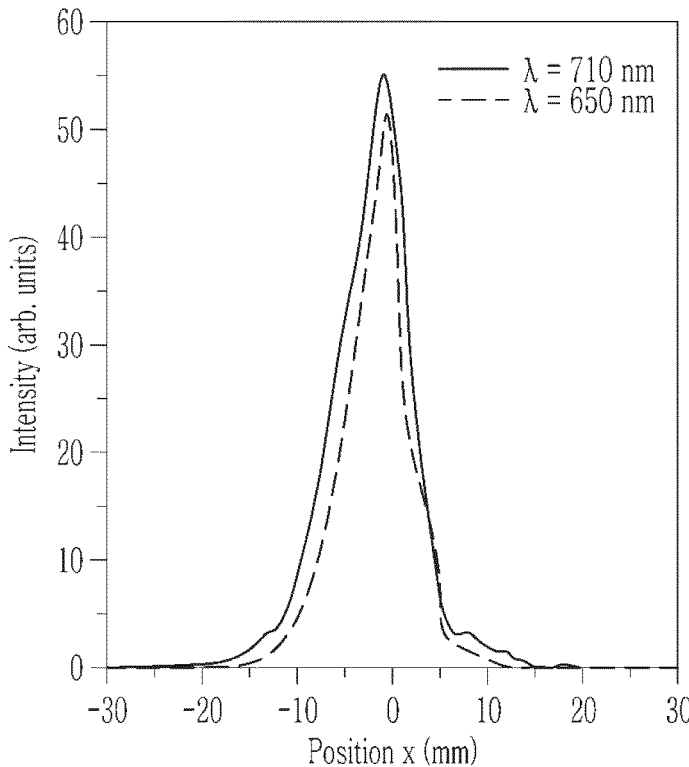
FIG. 16 is a graph showing signals obtained from first and second photo-detecting elements of the bio imaging system according to Example 2.
Figure 17:
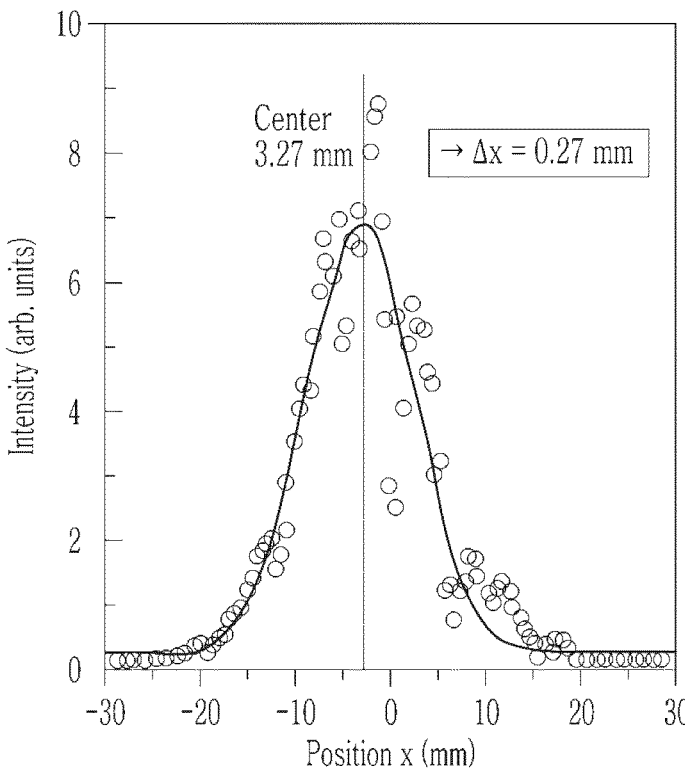
FIG. 17 is a graph obtained by separating and extracting the difference between the signals of the first and second photo-detecting elements shown in FIG. 16.

The results are shown in FIGS. 16 and 17.

FIG. 16 is a graph showing signals obtained from first and second photo-detecting elements of the bio imaging system according to Example 2, and FIG. 17 is a graph obtained by separating and extracting the difference between the signals of the first and second photo-detecting elements shown in FIG. 16.

Referring to FIGS. 16 and 17, differences of the signals obtained from the first photo-detecting element having an absorption peak wavelength of 650 nm and the second photo-detecting element having an absorption peak wavelength of 710 nm are analyzed to separate a lower blood vessel image and an upper blood vessel image and thus extract the lower blood vessel image. Specifically, the signal differences are analyzed and Gaussian-fitted to identify a center position, which has an x coordinate of 3.27 mm, and when compared with 3.0 mm of the position of the lower blood vessel BV2, the upper blood vessel BV1 is identified with an error of about 10% (0.27 mm). Accordingly, the signal differences with respect to different wavelengths are used to exclude the upper blood vessel BV1 on an x coordinate of 0 mm and extract the image of the lower blood vessel BV2.

Example 3

A simulation evaluation is performed under the same condition as Example 2 except that $x=3$ mm of the lower blood vessel BV2 is changed into $x=5$ mm.

Figure 18:
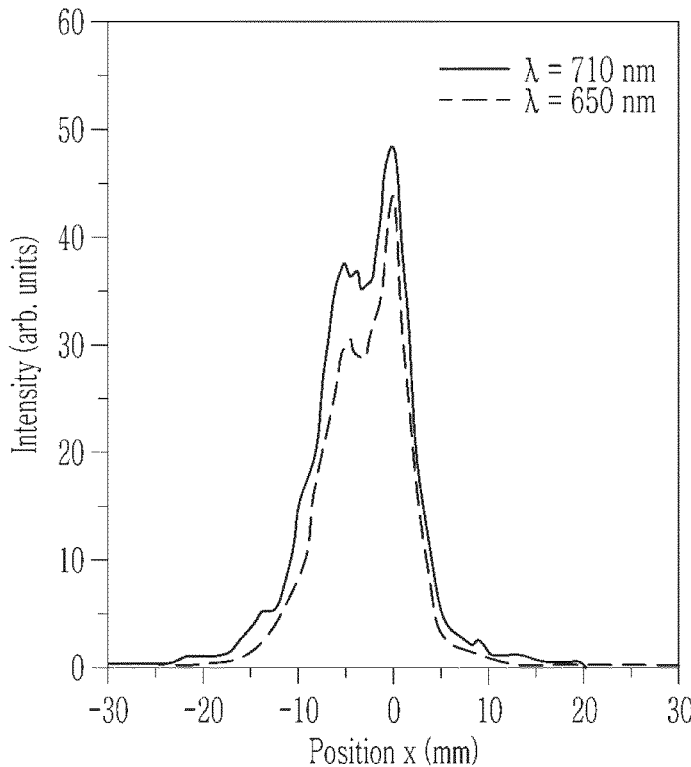
FIG. 18 is a graph showing signals obtained from first and second photo-detecting elements of the bio imaging system according to Example 3.
Figure 19:
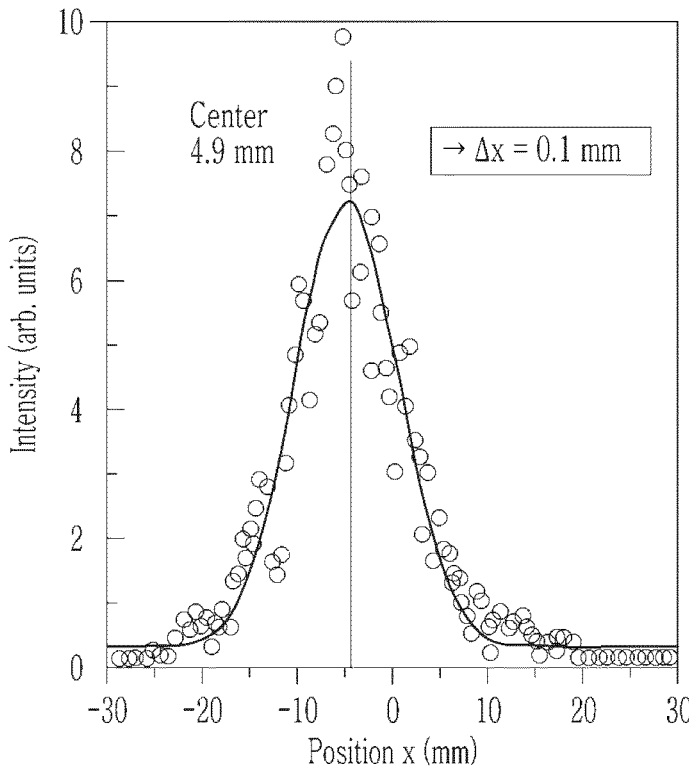
FIG. 19 is a graph obtained by separating and extracting the difference between the signals of the first and second photo-detecting elements shown in FIG. 18.

The results are shown in FIGS. 18 and 19.

FIG. 18 is a graph showing signals obtained from first and second photo-detecting elements of the bio imaging system according to Example 3, and FIG. 19 is a graph obtained by separating and extracting the difference between the signals of the first and second photo-detecting elements shown in FIG. 18.

Referring to FIGS. 18 and 19, differences of the signals obtained from the first photo-detecting element having an absorption peak wavelength of 650 nm and the second photo-detecting element having an absorption peak wavelength of 710 nm are analyzed to separate a lower blood vessel image from an upper blood vessel image and thus extract the lower blood vessel image. Specifically, the signal differences are Gaussian-fitted to identify a center position, which has an x coordinate of 4.9 mm, and when compared with 5.0 mm of the lower blood vessel BV2, the upper blood vessel BV1 is identified with an error of about 5% (0.1 mm). Accordingly, the signal differences with respect to different wavelengths are used to exclude the upper blood vessel BV1 on the x coordinate of 0 mm and extract the image of the lower blood vessel BV2.

Optical Simulation III

Example 4

Simulation conditions are as follows:

Light emitter-sensor array shown in FIGS. 1 and 2

Stretchable substrate thickness: 0.02 mm

Light emitter: surface light emitter (Plane light emitter, Lambertian)

Emission spectrum of light emitter: 500 nm to 900 nm

Upper electrode/lower electrode of light emitter: reflecting electrode/light-transmitting electrode Number of stacked photo-detecting elements: 3 (lower, middle, upper)

Absorption peak wavelength of lower photo-detecting element: 600 nm

Upper electrode/lower electrode of lower photo-detecting element: light-transmitting electrode/light-transmitting electrode Absorption peak wavelength of middle photo-detecting element: 700 nm Upper electrode/lower electrode: light-transmitting electrode/light-transmitting electrode of middle photo-detecting element Absorption peak wavelength of upper photo-detecting element: 800 nm Upper electrode/lower electrode of upper photo-detecting element: light-transmitting electrode/light-transmitting electrode Internal quantum efficiency of lower, middle, and upper photo-detecting elements is assumed to be 100%

Skin composition: skin thickness of 1.5 mm, fat thickness of 5 mm, muscle thickness of 30 mm, Information of upper blood vessel BV1: $x=0$ mm (ref.), $z=1.5$ mm (depth from skin surface), radius of 0.5 mm, Information of middle blood vessel BV3: $x=4$ mm, $z=5$ mm (depth from skin surface), radius of 1.5 mm, and Information of lower blood vessel BV2: $x=-3$ mm, $z=6$ mm (depth from skin surface), radius of 1.0 mm.

Figure 20:
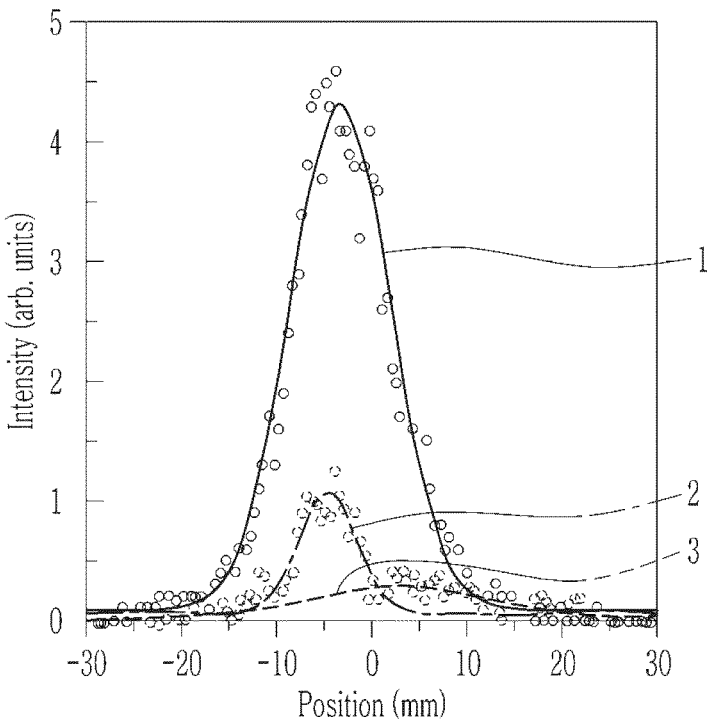
FIG. 20 is a graph showing signals obtained from stacked lower, middle, and upper photo-detecting elements of the bio imaging system according to Example 4.

The results are shown in FIG. 20.

FIG. 20 is a graph showing signals obtained from stacked lower, middle, and upper photo-detecting elements of the bio imaging system according to Example 4.

Referring to FIG. 20, differences of the signals of the lower photo-detecting element having an absorption peak wavelength of 600 nm, the middle photo-detecting element having an absorption peak wavelength of 700 nm, and the upper photo-detecting element having an absorption peak wavelength of 800 nm are analyzed to extract each lower, middle, and upper blood vessel image. Specifically, the longer the wavelength, the deeper the light is transmitted and reflected into the skin, and accordingly, signals at the wavelength of 600 nm may mainly include information of the upper blood vessel BV1, signals at the wavelength of 700 nm may mainly include information of the upper blood vessel BV1 and the blood vessel BV3, and signals at the wavelength of 800 nm may mainly include information of the upper blood vessel BV1, the middle blood vessel BV3, and the lower blood vessel BV2. In FIG. 20, Graph 1 shows signal differences at the wavelength of 800 nm and the wavelength of 700, and these signal differences are Gaussian-fitted to identify a center position, which may be used to obtain information of the lower blood vessel BV2 at x=−3 mm.

Likewise, in FIG. 20, Graphs 2 and 3 show signal differences at the wavelength of 800 nm and the wavelength of 600 nm, and these signal differences are Gaussian-fitted to separate two signals due to mixed information on x=−3 mm and x=4 mm and thus obtain information of the blood vessel BV3. Accordingly, signals differences at a plurality of wavelengths may be used to extract blood vessel information at a particular depth and imaged with (the number of wavelengths—1) image spatial resolutions.

While this disclosure has been described in connection with what is presently considered to be practical example embodiments, it is to be understood that the inventive concepts are not limited to the disclosed example embodiments. On the contrary, the inventive concepts are intended to cover various modifications and equivalent arrangements included within the spirit and scope of the appended claims.

What is claimed is:

1. A bio imaging system, comprising:
a stretchable substrate;
a plurality of light emitters on the stretchable substrate, each light emitter of the plurality of light emitters being configured to irradiate light; and
a plurality of sensors on the stretchable substrate, each sensor of the plurality of sensors being configured to detect light scattered or reflected by internal tissue of a living body,
wherein each sensor of the plurality of sensors includes a plurality of photo-detecting elements overlapped in a thickness direction of the stretchable substrate and having different absorption peak wavelengths in relation to each other,
wherein each emission spectrum of each light emitter of the plurality of light emitters includes all of respective absorption spectra of the plurality of photo-detecting elements, and
wherein the bio imaging system further includes processing circuitry configured to obtain electrical signals from the plurality of photo-detecting elements and to generate a three-dimensional image of the internal tissue of the living body based on combining a plurality of depth images according to the electrical signals obtained from the plurality of photo-detecting elements,
wherein the stretchable substrate comprises a plurality of first regions having a first elastic modulus and a second region between adjacent first regions of the plurality of first regions, the second region having a second elastic modulus, the first elastic modulus being higher than the second elastic modulus,

wherein the plurality of light emitters and the plurality of sensors are on separate, respective first regions of the plurality of first regions of the stretchable substrate, such that each separate first region is overlapped in the thickness direction of the stretchable substrate with one of:
a separate sensor of the plurality of sensors, or
a separate light emitter of the plurality of light emitters,
wherein each sensor of the plurality of sensors includes a first photo-detecting element and a second photo-detecting element overlapped in the thickness direction, wherein:
the first photo-detecting element includes a first absorption layer and a first electrode, the first absorption layer configured to selectively detect light in a first absorption spectrum having a first absorption peak wavelength, and
the second photo-detecting element includes a second absorption layer and a second electrode, the second absorption layer configured to selectively detect light in a second absorption spectrum having a second absorption peak wavelength, the second absorption peak wavelength being longer than the first absorption peak wavelength,
the first electrode and the second electrode are overlapped with each other in the thickness direction,
the first absorption layer and the second absorption layer are both overlapped between the first electrode and the second electrode in the thickness direction, and
each sensor further includes a third electrode, the third electrode is a common electrode of the first photo-detecting element and the second photo-detecting element of the sensor, the third electrode is overlapped between the first electrode and the second electrode of the sensor in the thickness direction, the third electrode further overlapped between the first absorption layer and the second absorption layer of the sensor in the thickness direction.

2. The bio imaging system of claim 1, wherein each absorption peak wavelength of the plurality of photo-detecting elements is within a visible wavelength spectrum and an infrared wavelength spectrum.

3. The bio imaging system of claim 2, wherein each absorption peak wavelength of the plurality of photo-detecting elements is within 450±45 nm to 1200±120 nm.

4. The bio imaging system of claim 3, wherein a difference between absorption peak wavelengths of the plurality of photo-detecting elements is greater than or equal to 10±1 nm.

5. The bio imaging system of claim 1, wherein the plurality of light emitters are configured to emit light of same emission spectrum as each other.

6. The bio imaging system of claim 1, wherein the bio imaging system comprises
a light emitter-sensor array in which the plurality of light emitters and the plurality of sensors are alternately arranged.

7. The bio imaging system of claim 1, further comprising:
an encapsulation film covering the plurality of the light emitters and the plurality of sensors.

8. The bio imaging system of claim 1, further comprising:
a display panel.

9. A bio imaging method, comprising:
fixing the bio imaging system of claim 1 on skin of the living body, activating the plurality of light emitters of the bio imaging system to irradiate light to the skin of the living body, and selectively sensing light scattered or reflected by the internal tissue of the living body through the skin of the living body in each photo-detecting element of the plurality of photo-detecting elements of at least one sensor of the plurality of sensors of the bio imaging system according to a wavelength spectrum of the light scattered and reflected to obtain a plurality of images.

10. The bio imaging method of claim 9, further comprising:

extracting differences between the plurality of images to obtain the plurality of depth images of the internal tissue of the living body according to depth from a surface of the skin.

11. The bio imaging method of claim 10, further comprising:

combining the plurality of depth images of the internal tissue of the living body to generate the three-dimensional image of the internal tissue of the living body.

12. The bio imaging method of claim 9, wherein the internal tissue of the living body includes a blood vessel.

13. A bio imaging system, comprising:

a stretchable substrate;

a plurality of light emitters on the stretchable substrate, each light emitter of the plurality of light emitters being configured to irradiate light; and a plurality of sensors on the stretchable substrate, each sensor of the plurality of sensors being configured to detect light scattered or reflected by internal tissue of a living body, wherein each sensor of the plurality of sensors includes a plurality of photo-detecting elements overlapped in a thickness direction of the stretchable substrate and having different absorption peak wavelengths in relation to each other, wherein each emission spectrum of each light emitter of the plurality of light emitters includes all of respective absorption spectra of the plurality of photo-detecting elements, and wherein the bio imaging system further includes processing circuitry configured to obtain electrical signals from the plurality of photo-detecting elements and to generate a three-dimensional image of the internal tissue of the living body based on combining a plurality of depth images according to the electrical signals obtained from the plurality of photo-detecting elements, wherein the stretchable substrate comprises a plurality of first regions having a first elastic modulus and a second region between adjacent first regions of the plurality of first regions, the second region having a second elastic modulus, the first elastic modulus being higher than the second elastic modulus, wherein the plurality of light emitters and the plurality of sensors are on separate, respective first regions of the plurality of first regions of the stretchable substrate, such that each separate first region is overlapped in the thickness direction of the stretchable substrate with one of:

a separate sensor of the plurality of sensors, or a separate light emitter of the plurality of light emitters, wherein each sensor of the plurality of sensors includes:

a first photo-detecting element including a first absorption layer overlapped between a first electrode and a second electrode in the thickness direction, the first absorption layer configured to selectively detect light in a first absorption spectrum having a first absorption peak wavelength, a second photo-detecting element stacked on the first photo-detecting element in the thickness direction, the second photo-detecting element including a second absorption layer overlapped between a third electrode and a fourth electrode in the thickness direction, the second absorption layer configured to selectively detect light in a second absorption spectrum having a second absorption peak wavelength, the second absorption peak wavelength being longer than the first absorption peak wavelength, a third photo-detecting element stacked on the second photo-detecting element in the thickness direction such that the second photo-detecting element is overlapped between the first photo-detecting element and the third photo-detecting element in the thickness direction, the third photo-detecting element including a third absorption layer overlapped between a fifth electrode and a sixth electrode in the thickness direction, the third absorption layer configured to detect light in a third absorption spectrum having a third absorption peak wavelength, the third absorption peak wavelength being longer than the second absorption peak wavelength, and a plurality of insulating layers, the plurality of insulating layers including:

a first insulating layer overlapped between the first photo-detecting element and the second photo-detecting element in the thickness direction, and a second insulating layer overlapped between the second photo-detecting element and the third photo-detecting element in the thickness direction.

14. The bio imaging system of claim 13, wherein each absorption peak wavelength of the plurality of photo-detecting elements is within a visible wavelength spectrum and an infrared wavelength spectrum.

15. The bio imaging system of claim 14, wherein each absorption peak wavelength of the plurality of photo-detecting elements is within 450±45 nm to 1200±120 nm.

16. The bio imaging system of claim 13, wherein the plurality of light emitters are configured to emit light of same emission spectrum as each other.

17. The bio imaging system of claim 13, wherein the bio imaging system further comprising:

a light emitter-sensor array in which the plurality of light emitters and the plurality of sensors are alternately arranged.

18. The bio imaging system of claim 13, further comprising:

an encapsulation film covering the plurality of the light emitters and the plurality of sensors.

19. The bio imaging system of claim 13, further comprising:

a display panel.

20. A bio imaging method, comprising:

fixing the bio imaging system of claim 7 on skin of the living body, activating the plurality of light emitters of the bio imaging system to irradiate light to the skin of the living body, selectively sensing light scattered or reflected by the internal tissue of the living body through the skin of the living body in each photo-detecting element of the plurality of photo-detecting elements of at least one sensor of the plurality of sensors of the bio imaging system according to a wavelength spectrum of the light scattered and reflected to obtain a plurality of images, and extracting differences between the plurality of images to obtain the plurality of depth images of the internal tissue of the living body according to depth from a surface of the skin, wherein the obtaining of the plurality of depth images of the internal tissue of the living body according to the depth from the surface of the skin includes:

extracting a first depth image of the internal tissue of the living body at a first depth from the surface of the skin, from a first difference between a first image obtained by the first photo-detecting element and a second image obtained by the second photo-detecting element, and extracting a second depth image of the internal tissue of the living body at a second depth that is deeper than the first depth, from a second difference between a third image obtained by the third photo-detecting element and the second image obtained by the second photo-detecting element.

*    *    *    *    *